United States Patent [19]

Ruth

[11] Patent Number: 4,948,882

[45] Date of Patent: Aug. 14, 1990

[54] SINGLE-STRANDED LABELLED OLIGONUCLEOTIDES, REACTIVE MONOMERS AND METHODS OF SYNTHESIS

[75] Inventor: Jerry L. Ruth, San Diego, Calif.

[73] Assignee: Syngene, Inc., San Diego, Calif.

[21] Appl. No.: 46,133

[22] Filed: May 4, 1987

Related U.S. Application Data

[63] Continuation-in-part of Ser. No. 617,094, Feb. 22, 1984, abandoned, which is a continuation-in-part of Ser. No. 468,498, Feb. 22, 1983, abandoned.

[51] Int. Cl.$^5$ .................. C07H 19/073; C07H 19/10; C07H 19/173; C07H 19/20
[52] U.S. Cl. ........................................ 536/27; 536/28; 536/29; 435/6; 935/77; 935/78
[58] Field of Search ............................. 536/27, 28, 29

[56] References Cited

U.S. PATENT DOCUMENTS

| | | | |
|---|---|---|---|
| 4,500,707 | 2/1985 | Caruthers et al. | 536/27 |
| 4,678,667 | 7/1987 | Meares et al. | 424/85 |
| 4,711,955 | 12/1987 | Wand et al. | 536/29 |

OTHER PUBLICATIONS

D. E. Draper, Nucleic Acids Research, 12(2), 989–1002 (1984).

Primary Examiner—John W. Rollins
Assistant Examiner—L. Eric Crane
Attorney, Agent, or Firm—Pretty, Schroeder Brueggemann & Clark

[57] ABSTRACT

Substantially pure single-stranded oligonucleotides having a preselected sequence of not more than about 200 nucleotides, at least one of which is at a preselected position in the sequence and includes a base with a covalently attached linker arm containing or capable of binding at least one reporter group or solid support. A process for the chemical synthesis of the substantially pure single-stranded oligonucleotide and modified nucleosides useful in such synthesis are provided.

4 Claims, No Drawings

SINGLE-STRANDED LABELLED OLIGONUCLEOTIDES, REACTIVE MONOMERS AND METHODS OF SYNTHESIS

BACKGROUND OF THE INVENTION

This application is a Continuation-in-Part of Ser. No. 617,094, filed Feb. 22, 1984, which is a Continuation-in-Part of Ser. No. 468,498, filed Feb. 22, 1983, both now abandoned.

This invention relates generally to modified oligonucleotides of preselected sequence, and more specifically to single-stranded oligonucleotides including nucleotides modified for the attachment of detectable reporter groups or solid support.

Nucleic acids, which are the carriers of genetic information between generations, are composed of linearly arranged individual units called nucleotides. Each nucleotide has a sugar phosphate group to which is attached one of the pyrimidine or purine bases, adenine (A), thymine (T), uracil (U), guanine (G) or cytosine (C). In the native state, single-stranded nucleic acids form a double helix through highly specific bonding between bases on the two strands; A will bond only with T or U, G will bond only with C. Thus a double stranded nucleic acid will form where, and only where, the sequence of bases in the two strands is complementary.

The understanding of complementary bonding between nucleic acids permits a variety of applications. For example, labelled nucleic acids of known base sequence, termed genetic probes, may be used to detect the presence of complementary nucleic acid in a sample. Such technology provides the most sensitive method available for determining the existence of a particular gene in a cell or of organisms such as viruses and bacteria. The ideal genetic probe would be of uniform length to allow predictable hybridization behavior and would be of homogeneous sequence to minimize cross reactivity with non-targeted nucleic acids. Moreover, it would be single-stranded and easily detectable.

One factor which has limited the utilization of genetic probes has been the difficulties encountered in producing detectable single-stranded nucleic acids having a preselected sequence. Two techniques of nucleic acid synthesis are currently used: enzymatic and chemical, i.e. non-enzymatic. The enzymatic synthesis of nucleic acid requires preexisting DNA for a template and utilizes natural cellular enzymatic mechanisms to facilitate replication of DNA segments. Two conventional examples of such synthesis are the nick translation protocol (Rigby et al., 1977 *J. Mol. Biol.* 113:237–251) and the gap-filling reaction (Bourguignon et al., 1976. *J. Virol.* 20:290–306). In both methods, preexisting DNA is contacted with an enzyme known as a DNase which nicks the strand, causing a break between a 3'-hydroxyl group and the adjacent 5'-phosphate. Such nicked or gapped DNA then serves as both a template and a primer. In the presence of a DNA polymerase, such as POL I which is isolated from *E. coli*, free nucleotides are successively condensed on to the 3' hydroxyl group while nucleotides adjacent to the 5' end of the nick are simultaneously cleaved. Double-stranded DNA having new strands composed of the added nucleotides is thus formed. Although DNA polymerases are the enzymes most commonly used in such procedures, other enzymes such as terminal transferases, reverse transcriptases and RNA polymerases can also be used with similar results.

If one or more of the provided nucleotides are modified, for example to include a label, such modifications will be incorporated into the new strand. Only a limited array of modifications may be utilized in such a method, however, due to the interference of the modifications with the activity of the enzymes. Radioisotopes, such as $^{32}P$ or $^{14}C$, may be readily incorporated since they closely resemble the natural isotopes, and thus radioactively labelled probes have been widely used. Because of the potential hazards associated with handling and disposing of radioactive materials and their inherent instability, however, radioactive probes are undesirable.

Certain other modified bases have been incorporated into oligonucleotides prepared by enzymatic synthesis. Ward et al., European Patent Application No. 82301804.9 disclose pyrimidine and purine bases having certain moieties attached, such as biotin, which are capable of complexing with a polypeptide for detection. These modified bases can be incorporated into enzymatically produced nucleic acids. However, hybridization probes produced by such methods have inherent drawbacks which limit their usefulness. For example, enzymatic synthesis relies on nicked preexisting DNA to serve as a template. Because multiple nicks are introduced randomly in a single chain by contact with a DNase, double-stranded oligonucleotides of widely different composition, sequence, and length will be simultaneously produced. Length of product chains vary considerably, usually from 400 to 1000 bases in length. In general, chains of over 200 bases are termed "polynucleotides" while those under 200 bases are termed "oligonucleotides." Such enzymatic synthesis chains may reach a length of several thousand nucleotides but for practical purposes, they generally cannot be made less than about two hundred nucleotides in length. The absolute length cannot be controlled, however, and the product will be a heterologous mixture of lengths and sequences. No conventional method permits separation and purification of these heterogeneous pieces. Moreover, it is not possible to control the site at which the modified nucleotide is incorporated into the newly formed chain. While the identity of the particular nucleotide which is modified does determine that the label will be incorporated opposite a position of the complementary nucleotide in the template, the method does not permit the synthesis of a polynucleotide having modifications at particular preselected sites among those available. More importantly, the range of modifications of the nucleotides which can be incorporated is limited to those which will be recognized and incorporated by the enzymes.

To a limited extent, modifications to nucleic acids have also been introduced by post-synthetic modification of an enzymatically synthesized nucleic acid, such as by mercuration or palladium catalyzed addition reactions. Only cytosine residues are susceptible to such addition reactions, however; thymine and purine bases cannot be modified by this method. Moreover, as with enzymatic incorporation of modified bases, the particular site at which the modification may be introduced can not be preselected and both strands are randomly modified. Where the stoichiometry of the reaction is controlled so as to modify only a limited proportion of the available nucleotides, the modifications will be introduced randomly at sites appropriate to cytosine incorporation, thereby producing a heterogeneous population of modified nucleic acids; see Bigge, et al., (1981). *J. Carb. Nucleosides Nucleotide,* 8:259 (1981). Furthermore, it has been demonstrated that where the reaction conditions are intensified so as to modify substantially all available nucleotides, undesired chemical degradation of the oligonucleotide ensues. Dale et al., (1975). *Biochem.* 14:2447. This method has not been used to incorporate labels or reporter groups.

The prior art methods of enzymatic synthesis require double-stranded DNA as a template, and produce double-stranded nucleic acids having label incorporated in both strands. Moveover, the resulting nucleic acids are heterogenous, varying both in sequence, length, and in position of the modified bases. Enzymatic synthesis cannot produce a single stranded probe of preselected length, preselected sequence having unique reporter groups defined by site and number. Furthermore, the scope of modifications obtainable in the oligonucleotide product is severely restricted as the enzymes required for modification can only recognize and incorporate a very limited array of modified nucleotides in both strands of a double-stranded, nonuniform nucleic acid. As a result proteins, nucleic acids, carbohydrates, fluorophors, and lumiphors cannot be incorporated as labels by these methods.

Naturally occurring nucleotides may be condensed into single-stranded oligonucleotides of preselected sequence and length using chemical, or non-enzymatic, methods of synthesis. Such methods have been reviewed by Matteucci, et al., (1982). *J. Amer. Chem. Soc.* 103:3185. Chemical synthesis usually involves successive coupling of an activated nucleotide monomer and a free hydroxyl-bearing terminal unit of a growing nucleotide chain. The coupling is effected through a reactive phosphorous-containing group, such as a phosphate diester or more often, a phosphite triester. Phosphochloridite (Letsinger, et al., (1980). *J. Org. Chem.* 45:2715) and phosphoamidite (Caruthers, et al., U.S. Pat. No. 4,458,066) reactions are commonly used. Caruthers teaches the synthesis of oligonucleotides containing as many as 30 bases composed of only naturally-occurring nucleotides. However, no chemical synthesis of oligonucleotides incorporating modified bases or reporter groups of any type has been disclosed in the prior art.

Accordingly, there exists a long felt and compelling need for single-stranded oligonucleotides of preselected sequence and length having incorporated therein modified nucleotides capable of detection. Such modifications should be non-radioactive and preferably allow accurate and inexpensive detection. The present invention satisfies this need and provides related advantages as well.

SUMMARY OF THE INVENTION

The present invention provides a substantially pure single-stranded oligonucleotide comprising a preselected sequence of not more than about 200 nucleotides, at least one nucleotide of which located at a preselected position in the sequence, including a base with a covalently attached linker arm containing at least one reporter group or a solid support or a moiety capable of binding at least one reporter group or a solid support. The linker arm can be attached to the base at any position, including the C-5 position when the base is a pyrimidine and the C-8 position when the base is a purine. The reporter group can be capable of colorimetric, fluorescent, luminescent or antibody- or other ligand-mediated detection. The reporter group could also be a radioactive moiety. The oligonucleotide can be either an oligodeoxyribonucleotide or an oligoribonucleotide.

The invention further provides a process for the chemical synthesis of such substantially pure single-stranded oligonucleotides having at least one modified nucleotide which comprises the stepwise addition of reactive nucleotides in a preselected sequence to a substantially pure single-stranded oligonucleotide of less than 200 nucleotides, also having a preselected sequence. The addition is accomplished through a reactive phosphorous-containing group attached to a 3'- or a 5'-hydroxyl group. At least one of the nucleosides so added contains a base having a covalently attached linker arm containing, or capable of binding, a reporter group or solid support. The invention also provides modified nucleoside monomers useful in the above process.

DETAILED DESCRIPTION OF THE INVENTION

The present invention provides a substantially pure single-stranded oligonucleotide of preselected sequence, at least one nucleotide of which has a substituent group or linker arm which has bound or is capable of binding a detectable reporter group or solid support. The oligonucleotide of the present invention is non-enzymatically synthesized by the stepwise addition of a selected reactive nucleotide monomer and a free hydroxyl-bearing terminal unit of an oligonucleotide chain of preselected sequence, at least one nucleotide of the completed chain having a substituent group bound or capable of binding at least one reporter group or a solid support. The invention also provides reactive nucleotide monomers useful for the synthesis of the above-described oligonucleotides. Such monomers contain an active phosphorous-containing group at the 5'- or 3'-hydroxyl of a ribonucleoside or deoxyribonucleoside, a linker arm attached to the base and bound to or capable of binding a reporter group or solid support, and appropriate blocking groups on reactive sites. The incorporation of one or more such modified nucleotide into an oligonucleotides results in a modified oligonucleotide.

The nucleotide units in the modified oligonucleotide of the present invention can be purine or pyrimidine based, and can be ribonucleotides or deoxyribonucleotides. Such bases can take the form of the purines adenine (A), guanine (G) and hypoxanthine (H), or of the pyrimidines uracil (U), cytosine (C) or thymine (T). When reference is made herein to the use of purine or pyrimidine bases, such expressions are intended to include analogs of such bases. Among such analogs are the analogs of purine bases, such as amino-, aza- or deaza-adenosines (tubercidins, formycins, hypoxanthines, and the like), and the analogs of pyrimidine bases, such as deazauracil, deazacytosine, azauracils, azacytosines, and the like. Alternatively, any other base isolated from natural sources may be used.

The substituent groups or linker arms of the present invention which are capable of binding reporter groups can be generally characterized as nucleophilic. Exemplary of such linker arms are those which contain at least one reactive amino, carboxyl, hydroxyl and thio groups and the like.

In a preferred embodiment, the linker arm is attached to a sterically tolerant site on a nucleotide. A sterically tolerant site is defined as one where the attachment of the substituent group will not cause significant interference with either the hybridization of the modified oligonucleotide to a complementary nucleic acid segment or with the binding of the linker arm to a reporter group. Such sterically tolerant sites are found, for example, at C-8 position of a purine and the C-5 position of a pyrimidine base. Nucleotides having substituent groups bound at sites other than those which are sterically tolerant are also useful, however. For example, where only a portion of the probe is designed to hybridize with a targeted DNA segment, the linker arm may be located external to the area of complementarity without interfering with hybridization. Moreover, even if the linker arm is located within the hybridizing segment so as to prevent binding of the particular nucleotide to which it is attached, hybridization of the surrounding nucleotides may be sufficient to provide a useful probe.

A reporter group can be defined as a chemical group which has a physical or chemical characteristic which can be readily measured or detected by appropriate detector systems or procedures. Ready detectability can be provided by such characteristics as color change, luminescence, fluorescence, or radioactivity; or it can be provided by the ability of the reporter group to serve as a ligand recognition site. Such characteristics can be measured or detected, for example, by the use of conventional colorimetric, spectrophotometric, fluorometric or radioactivity sensing intrumentation, or by visual inspection.

The interactions which can be usefully initiated by the reporter group defined herein include appropriately specific and selective interactions productive of groups or complexes which are themselves readily detectable, for example, by colorimetric, spectrophotometric, fluorometric, or radioactive detection procedures. Such interactions can take the form of protein-ligand, enzyme-substrate, antibody-antigen, carbohydrate-lectin, protein-cofactor, protein-effector, nucleic acid-nucleic acid and nucleic acid-ligand interactions. Examples of such ligand-ligand interactions include dinitrophenyl-dinitrophenyl antibody, biotin-avidin, oligonucleotide-complementary oligonucleotide, DNA-DNA, RNA-DNA and NADH-dehydrogenase. Either one of each of such ligand pairs may serve as a ligand recognition type reporter group.

In the process of the present invention, a selected reporter group or groups can optionally be attached to the nucleotide monomer before coupling of the monomer to the terminal unit of the nucleotide chain, or can be attached to the product oligonucleotide after formation thereof. The sequence of the nucleotides in the product oligonucleotide is preselected to provide such oligonucleotide with the specificity necessary to hybridize with the targeted sequence.

The coupling step preferably involves coupling of a selected monomer unit activated at the 3' position with a free 5'-hydroxyl of the terminal unit of the growing nucleotide chain. Alternatively, such coupling can involve attaching a monomer unit activated at the 5' position with a free 3'-hydroxyl of the terminal unit of the nucleotide chain. The terminal unit can be the initial or only unit in the growing nucleotide chain at the time of coupling of the modified nucleotide monomer, or it can be the terminal nucleotide of an oligonucleotide having a preselected sequence.

The term "substantially pure," as used herein, is intended to include those oligonucleotides which have the preselected sequence of nucleotides and have linker arms at preselected locations in the sequence. Oligonucleotides of divergent sequence are excluded. However, the term is specifically intended to include those oligonucleotides comprising subsequences of the predetermined sequence which result from incomplete coupling of reactive nucleotides into the growing oligonucleotide chain. In practice, even under ideal conditions less than all molecules present will exist as the desired product. For example, when coupling a nucleotide monomer and a hexamer into a septamer, three moieties will be present after the reaction mixture is complete; the heptamer, the hexamer and the nucleotide monomer. While the majority of the reaction mixture will exist as the desired heptamer, a certain proportion will inevitably remain as one of the starting reagents. If necessary, these reagents can be separated from the desired oligonucleotide product by well-known methods such as high performance liquid chromotography and gel electrophoresis. Nonetheless, the presence of these artifacts of incomplete reaction are not intended to defeat the substantially pure nature of the modified oligonucleotide of the present invention. Furthermore, it is understood that the presence of unrelated chemical moieties such as solvents, buffers and other non-nucleic acid components do not diminish the substantially pure nature of the oligonucleotides.

The substantially pure single-stranded oligonucleotides of the present invention are useful tools in protocols involving nucleic acid hybridization techniques. Among such uses are the identification, localization, isolation or quantification of complementary nucleotide sequences of interest in cellular or cell-free systems. Such protocols can be used, for example, to detect the presence of nucleotide sequences which are either native or the result of infective agents. Infective agents can include viruses, bacteria, mycoplasmas, parasites, including Chlamydia and Rickettsia, and fungi. Such uses can also include diagnostic applications of any fundamental biological event detectable through hybridization of nucleic acid components, or immobilization or purification of complementary sequences by affinity chromatography when the product oligonucleotide is attached to a solid support.

The non-enzymatic synthetic process of the present invention produces preferred oligonucleotides of the following generic formula:

FORMULA I

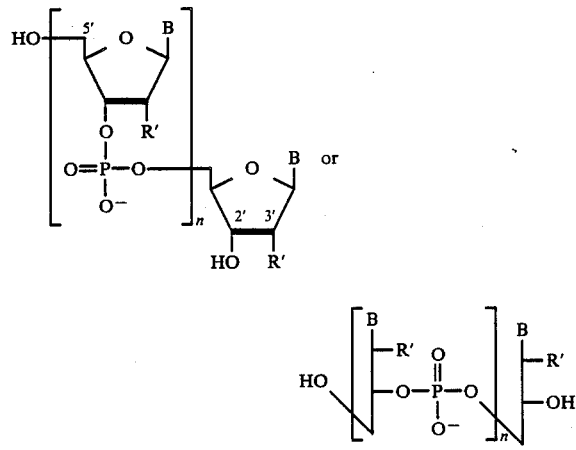

wherein n is 1 to about 199, preferably about 5 to about 60, and most preferably about 10 to about 40, R' is hydrogen or hydroxy, and B is any one of the purine or pyrimidine bases adenine, guanine, hypoxanthine, cytosine, uracil, thymine, or any other naturally occurring base, the nucleotide units having naturally occurring bases being independently intermixed with one or more nucleotide units having modified bases ($B^m$). The modified pyrimidine bases ($Py^m$) are substituted preferably but not exclusively at the C-5 position, and typical examples thereof are the uracil and cytosine bases illustrated by the following generic formulas:

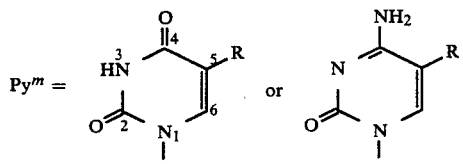

modified uracil base    modified cytosine base

The modified purine bases ($Pu^m$) are preferably but not exclusively substituted at the C-8 position, and typical examples thereof are the modified adenine and guanine bases illustrated by the following generic formulas

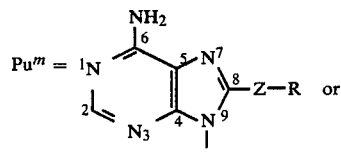

modified adenine base

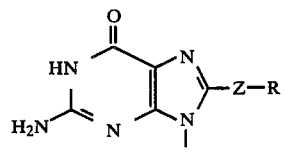

modified guanine base

The substituent group or linker arm R is characterized by its ability to bind or be composed of one or more reporter groups or solid supports. In the modified pyrimidine bases the linker arm R generally comprises two or more carbon atoms, whereas in the modified purine bases R generally comprises one or more carbon atoms. In this context, R preferably takes the form of one of the following functionalized carbon chains:

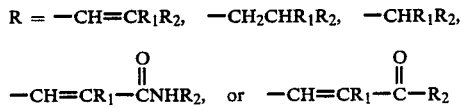

wherein $R_1$ is hydrogen or alkyl; $R_2$ is alkyl, alkenyl, aryl, or functionalized alkyl, alkenyl, aryl wherein functional groups include one or more amines, amides, nitriles, carboxylic acids and esters, hydroxyls, sulfonates, or the like; and Z is a polyvalent heteroatom such as nitrogen, oxygen or sulfur.

$R_2$ contains the site of the attachment of the bases to a solid support, or to one or more reporter groups which function, for example, as a colorimetric, fluorescent, luminescent, radioactive, or ligand recognition group. Functionally fluorescent groups include fluoresceins, rhodamines, and the like, or proteins capable of producing fluorescence; functionally luminescent groups include luminols, acridines, luciferins, dioxetanes, dioxamides, and the like, or proteins capable of producing luminescence. Ligand recognition groups include vitamins (such as biotin or adducts thereof, including iminobiotin and desthiobiotin), antigens such as dinitrophenyl, amino benzenesulfonates, carbohydrates and other functional groups or adducts of such groups which can be recognized by ligand-like interactions with proteins, or from which such ligand-like interactions can be elicited. A second oligonucleotide capable of specific interaction with the first oligonucleotide is illustrative of a group from which a ligand-like interaction can be elicited. Ligand recognition groups can also serve as functionally colorimetric reporter groups when recognition results in dye formation. For example, when dinitrophenyl is used as a reporter group, known detection systems using an anti-dinitrophenyl antibody coupled to peroxidase can be used as a detection system, resulting in a color change. Functionally radioactive groups incorporate a radioactive element in the chosen reporter group, or a protein capable of producing a useful radioactive product.

Oligonucleotides of Formula I are prepared by chemical synthesis from monomer nucleotide analog units of the formula:

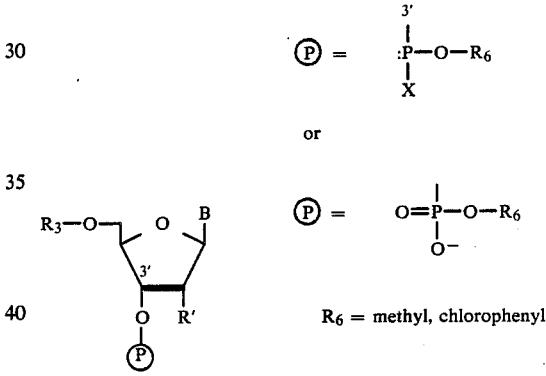

FORMULA II    X = chloro, dialkylamino, morpholino wherein $R_3$ is trityl (triphenylmethyl), dimethoxytrityl, or another appropriate masking group for the 5'-hydroxyl; B and R' are masked, if appropriate; and ⓟ represents a phosphorus-containing group suitable internucleotide bond formation during chain extension in synthesis of a product oligonucleotide. The phosphorus-containing groups ⓟ suitable for internucleotide bond formation are preferably alkyl phosphomonochloridites or alkyl phosphomonoamidites. Alternatively phosphate triesters can be employed for this purpose. The monomer unit can alternatively have $R_3$ attached at the 3'-hydroxyl and ⓟ attached at the 5'-hydroxyl.

Generally, the term "masking group" or "blocking group" is a functional expression referring to the chemical modification or "blocking" of an integral functional group by attachment of a second moiety to disguise the chemical reactivity of the functional group and prevent it from reacting in an undesired manner during reactions at other sites in the molecule. Such modification is reversible, and allows subsequent conversion back to the original functional group by suitable treatment. In many cases, such masking formally interconverts structural functionality, e.g., a primary amine masked by acetylation becomes a substituted amide which can be later converted back to the primary amine by appropriate hydrolosis.

The compounds of Formula I include the acceptable conjugate acid salts thereof. Conjugate acids which may be used to prepare such salts are those containing nonreactive cations and include, for example, nitrogen-containing bases such as ammonium salts, mono-, di-, tri-, or tetra-substituted amine salts, and the like, or suitable metal salts such as those of sodium, potassium, and the like.

The process steps of the present invention will now be generally described and illustrated diagrammatically. Thereafter, the invention will be illustrated more specifically and detailed examples thereof provided. Since the invention relates to oligonucleotides incorporating both pyrimidine-based and purine-based nucleotide units, the use of both pyrimidine and purine-based compounds in the synthetic process will be illustrated. The specific pyrimidine and purine-based compounds illustrated are only exemplary of the respective pyrimidine and purine classes, and it is to be understood that any other member of the respective class can be substituted therefore in the process and the product oligonucleotide, whenever suitable or desired. While deoxyribonucleotide compounds are shown for the most part, it is understood that ribonucleotide compounds are also contemplated by the invention and can be substituted for the deoxyribonucleotide compounds wherever ribonucleotide compounds are desired in the product oligonucleotide.

The reactive nucleotide monomers of this invention are essential as intermediates in the process for synthesizing the new oligonucleotides. These reactive nucleotide monomers are represented by the following structure

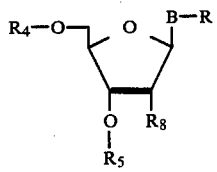

Wherein B is a pyrimidine or purine base; R is a linker arm containing or, when unblocked, capable of binding at least one reporter group or a solid support; and provided that when $R_4$ is a masking group, then $R_5$ is either a reactive phosphorous-containing group or H if the 5'-OH group of the 5'-terminal nucleotide of a growing oligonucleotide contains a reactive phosphorous-containing group; and when $R_5$ is masking group then $R_4$ is either reactive phosphorous-containing group or H if the 3'-OH of the 3'-terminal nucleotide of a growing oligonucleotide contains a reactive phosphorous-containing group; and $R_8$ is H or a masked hydroxyl group.

Such reactive nucleotide monomers each have a base which is modified by a linker arm comprising a functionalized carbon chain incorporating at least the functional group as aforedescribed, preferably including one or more amides, the nitrogen of the amides being preferably attached to a sterically tolerant site on the base through the carbon chain. In the case of pyrimidine-based nucleotides, the carbon chain is preferably attached at the C-5 position, and in the case of the purine-based nucleotides, the carbon chain is preferably attached at the C-8 position though a polyvalent hetero-atom, such as nitrogen, oxygen or sulfur. In addition such nucleotides are chemically blocked at the 5' position (or the 3' position) with a group, such as dimethoxytrityl, appropriate for the chemical synthesis of oligonucleotides.

In the new class of nucleotide the linker arm R can be chosen from $-CH_2CHR_1C_nH_{2n}Y$, $-CH=CR_1C_nH_{2n}Y$, $-CHR_1C_nH_{2n}Y$, $-CH=CR_1-\overset{O}{\underset{\|}{C}}-NHC_nH_{2n}Y$, or $-CH=CR_1\overset{O}{\underset{\|}{C}}C_nH_{2n}Y$;

wherein $R_1$ is hydrogen or $C_{1-6}$ lower alkyl, n is 0 to 20 and Y contains at least one blocked amino or blocked carboxyl or blocked hydroxy or blocked thio group or at least one reporter group or solid support (i.e. $C_nH_{2n}Y = R_2$). More specifically Y can include one or more dinitrophenyl, or $-\overset{O}{\underset{\|}{NHCCX_3}}$ wherein X is hydrogen, fluorine or chlorine. The amino, carboxyl, hydroxy, and thio groups in Y are blocked because of the presence of the active phosphorous-containing groups at positions $R_4$ or $R_5$. Synthesis of these nucleosides, as well as of the masked forms thereof, is described hereinafter in Examples I, through XV, XXIX, XXX.

Preferred nucleosides incorporate the substituent group $-CH=CH\overset{O}{\underset{\|}{C}}-NHC_nH_{2n}Y$ at C-5 of pyrimidine nucleosides wherein n=3 to 12 and Y is $-\overset{O}{\underset{\|}{NHCCX_3}}$.

Most preferred are such nucleosides wherein the pyrimidine base is uracil.

The process of the present invention for preparing the modified oligonucleotide can be initiated by the preparation of the selected nucleoside. Generally, the most preferred nucleosides are best prepared in the following manner. 5-(Methyl 3-acrylyl)-2'-deoxyuridine is prepared from 2'-deoxyuridine by the method of Bergstrom and Ruth, (1976). *J. Amer. Chem. Soc.* 96:1587. The nucleoside is then treated with 1.05 equivalents of dimethoxytrityl chloride in pyridine for 4 hours to block the 5'-hydroxyl with dimethoxytrityl (DMT). The resulting product is purified by silica chromatography eluting a gradient of 0–10% methanol in chloroform containing 2% triethylamine. The purified 5'-DMT-5-(methyl 3 acrylyl)-2'-deoxyuridine is treated with 1N KOH for 24 hours at ambient temperature to hydolyze the methyl ester. The resulting 5'-DMT-5-(3-acrylyl)-2'-deoxyuridine is treated with excess dicyclohexylcarbodiimide and hydroxybenztriazole in pyridine. After 4 hours, a 2 to 5 fold excess of 1,7-diaminoheptane is added, and the reaction stirred overnight. After 12 to 20 hours, a 10 to 20 fold excess of trifluoroacetic anhydride is added, and the reaction stirred at room temperature for 4 hours. The product is purified by silica chromatography eluting a gradient of 0 to 10% methanol in chloroform containing 2% triethylamine, followed by exclusion chromatography using Sephadex LH-20 eluting 1% triethylamine in methanol. Appropriate fractions are combined to yield 5'DMT-5-[N-(7-trifluoroacetylaminoheptyl)-1-acrylamido]-2'-deoxyuridine; such product is appropriate for oligonucleotide synthesis by the phosphochloriditie procedure described in Examples XV and XVIII. Alternatively, such a compound can be prepared by the combination of methods described in Examples II and III. Replacing diaminoheptane in this process with other diaminoalkanes (e.g., diaminopropane, diaminohexane, diaminododecane) is productive of other compounds of varying substituent length wherein n=3, 6, or 12 and

Two such nucleosides, one pyrimidine (uracil)-based and the other purine (adenine)-based, are shown at the top of the diagram below illustrating the process. Reactive sites on the bases of the nucleosides are then masked, as shown in Reaction 1, by attachment of, for example, a benzoyl group (Bz) to the amine at the 6 position of the adenine-based nucleoside. Such masking is generally described in "Synthetic Procedures in Nucleic Acid Chemistry", Vol. 1, W. Zorbach and R. Tipson eds. (Wiley - Interscience, N.Y.) (1968). Unprotected amines on the substituent group are masked, for example, by attachment thereto of trifluoroacetyl groups (Ac), as also shown in Reaction 1.

It is important for the purposes of this invention to have appropriate blocking or masking groups for the functional moiety on the linker arm. These blocking groups must be substantially stable towards all chemical steps used in the synthesis of the oligonucleotide, but be capable of selective removal or deblocking, without degradation of the functional moiety or the oligonucleotide.

The selected 3'- or 5'-hydroxyl of the nucleoside is then masked by attachment thereto of a dimethoxytrityl (DMT) group. In Reaction 2 illustrated below, the 5'-hydroxyl is masked, leaving the 3'-hydroxyl free or available for reaction. Alternatively, the 3'-hydroxyl could be masked, leaving the 5'-hydroxyl free.

The nucleoside is then converted to an activated nucleotide monomer, preferably by attachment to its 3' hydroxyl of a phosphorus-containing group which includes an activating moiety. When the modified nucleoside is properly blocked, modifications of the procedures described by Letsinger, et al., Matteucci, et al., or as reviewed by Narang, et al. can be utilized for oligonucleotide synthesis. The use of phosphochloriditie chemistry such as that disclosed by Letsinger, et al., is detailed in Examples XVI-XVIII. In order to use phosphoamidite chemistry, a modification of the procedure of Beaucage and Caruthers is used as described in Examples XXIX and XXX, by phosphitylating the protected modified nucleoside with methyl chloro (N, N-diisopropyl) phosphoamidite or methyl chloro phosphomorpholidite, as in the improved procedure of Dorper, et al. (1983). *Nucleic Acids Res.* 11:2575. Alternatively, the protected modified nucleoside can be phosphorylated with 1.2 eq. chlorophenyl dichlorophosphate in trimethylphosphate at room temperature followed by quenching with water to give the 3'-chlorophenyl phosphate adduct of the modified nucleoside, such adducts being useful in a modification of the phosphotriester approach as illustratively reviewed by Narang, et al. The diagram illustrates in Reaction 3 the synthesis of activated monomer nucleotide units of Formula II by attachment to the nucleoside 3'-hydroxyl of a phosphomonochloridite group in which the chlorine functions as an activating moiety.

Coupling or condensation of the selected activated nucleotide monomer, i.e. the uracil-based monomer or the adenine-based monomer, to the terminal unit of a growing nucleotide chain is illustrated in Reaction 4 in the diagram. The nucleotide chain is shown as including in its right hand end a nucleotide unit having a naturally occurring base and having a solid support or masking group $R_4$ attached to its 3'-hydroxyl. The illustrated chain also includes one or more (n') nucleotide units having naturally-occurring bases, said units being coupled to the 5'-hydroxyl of the nucleotide unit, the terminal of one of the nucleotide units having a free hydroxyl at the 5' position. In the coupling reaction the chlorine of the monomer reacts with the hydrogen of the free hydroxyl of the terminal unit and is displaced, so that the oxygen of the terminal unit couples to the phosphorus of the monomer as shown, and the monomer thereby becomes the new terminal unit of the nucleotide chain.

The DMT 5' blocking group is then removed to permit further extension of the nucleotide chain by sequential coupling thereto of additional activated nucleotide monomer units. The nucleotide units added to the chain can be preselected and may have either naturally occurring or modified bases. The diagram shows in Reaction 4a the further extension of the chain by the addition of one or more (n") nucleotide units having naturally occurring bases.

When an oligonucleotide of the selected length and sequence has been synthesized, the DMT group can be removed from the terminal unit thereof, and the masked reactive groups are unmasked. Examples of modified uracil and adenine bases with their reactive groups unmasked are also shown diagrammatically at Reaction 5. If the initial nucleotide unit of the chain is bound to a solid support $R_4$, the chain is then generally removed from such solid support. The appropriate order of unmasking can be preselected.

Reporter groups $R_5$ appropriate for the intended use of the product oligonucleotide can then be bound to such substituent groups as exemplified in Reaction 6, which illustrates the respective bases with reporter groups $R_5$ bound to the respective substituent groups thereof.

Illustration of Synthetic Process
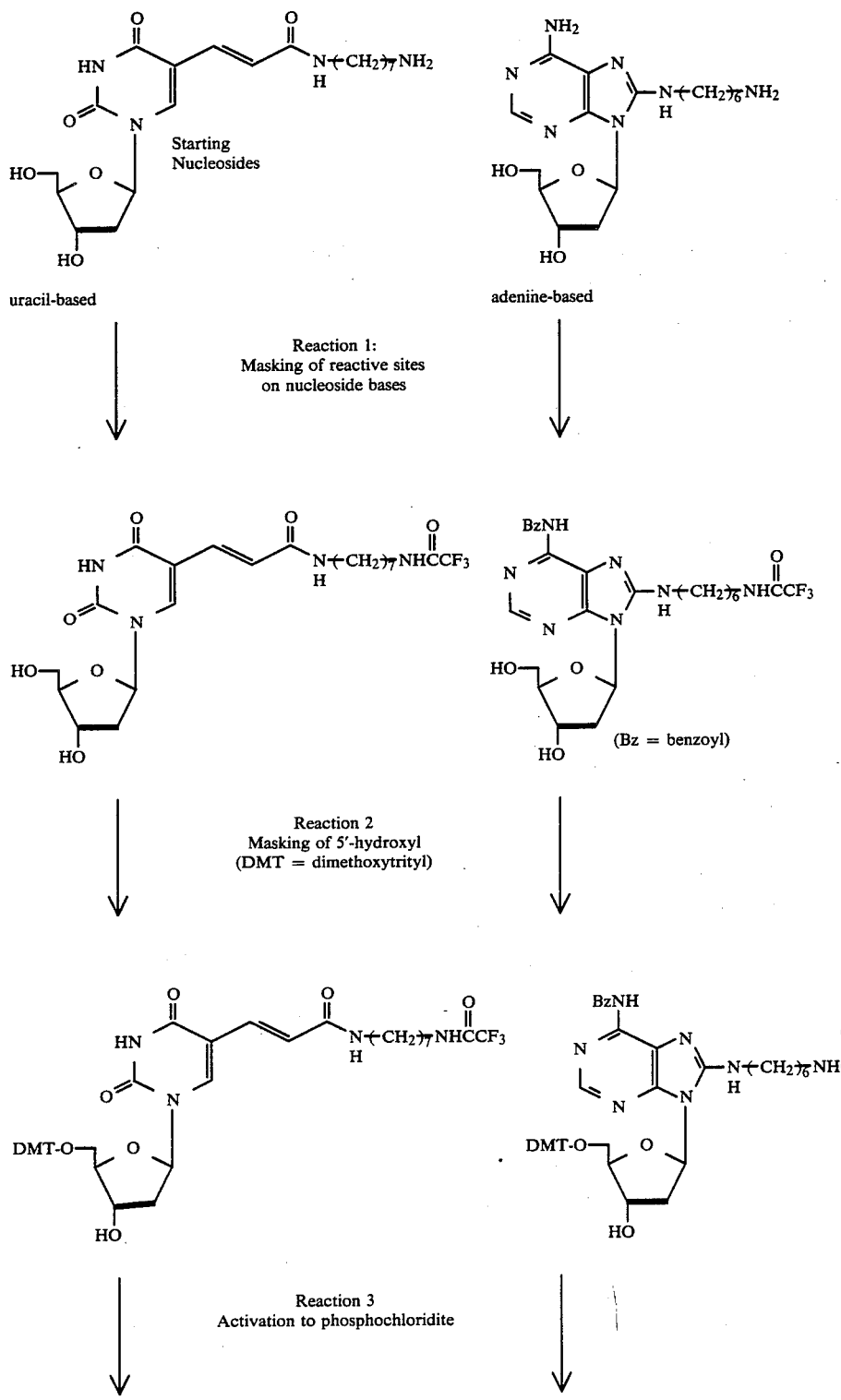

-continued
Illustration of Synthetic Process
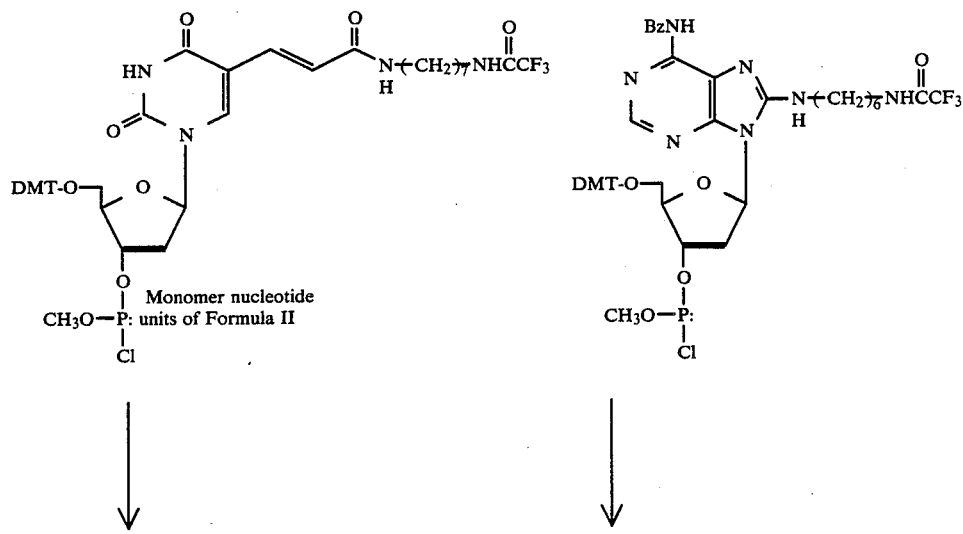
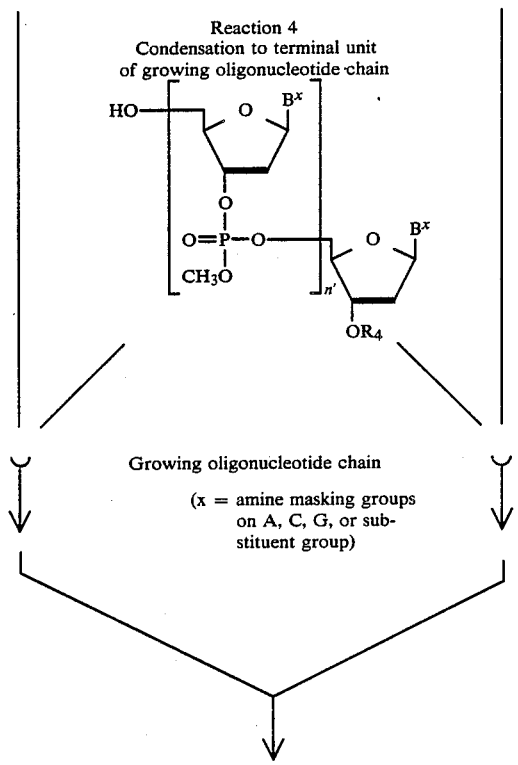
Reaction 4
Condensation to terminal unit
of growing oligonucleotide chain
Growing oligonucleotide chain
(x = amine masking groups on A, C, G, or substituent group)

-continued
Illustration of Synthetic Process
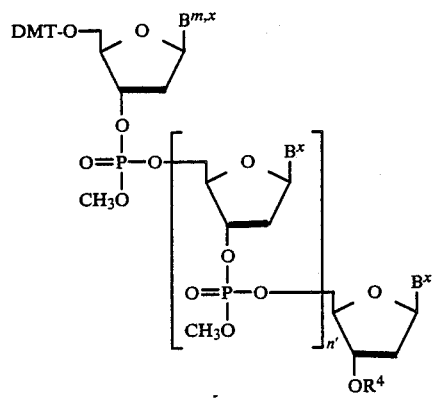
Reaction 4a
Further chain elongation (s)
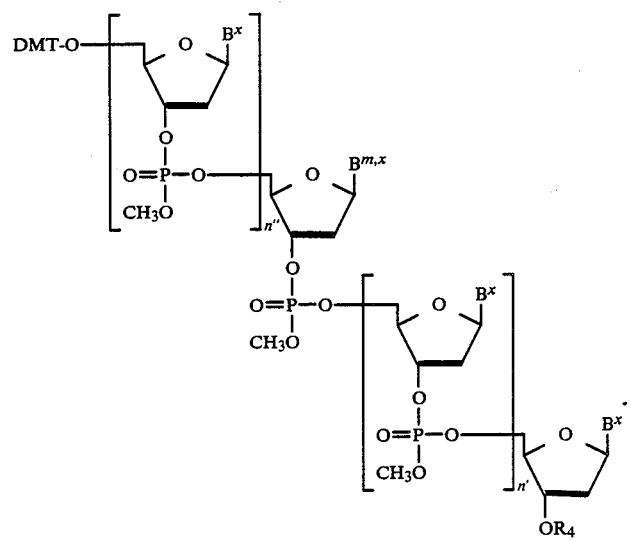
Reaction 5
Deblocking, unmasking, removal from $R_4$ -continued
Illustration of Synthetic Process

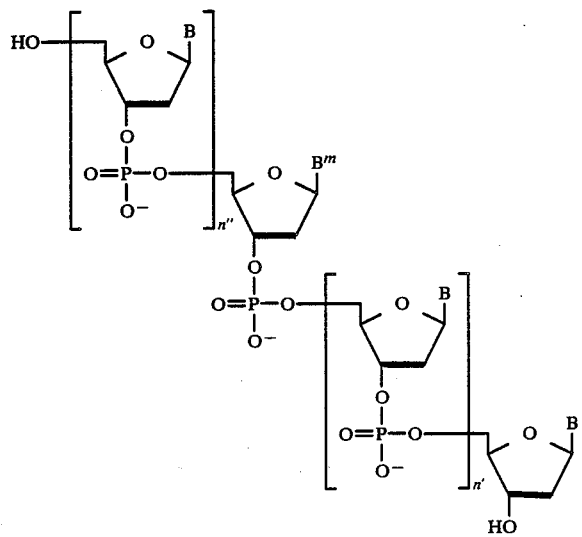

PRODUCT
OLIGONUCLEOTIDE
n' + n" = 0 to about 198
where $B^m$ = modified base (see pg 29)
where for example, $B^m$ in product oligonucleotide (pg 12) is:

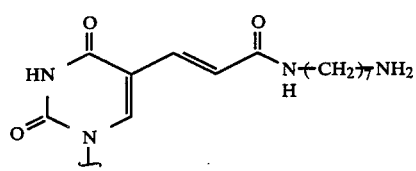

uracil base
(modified)

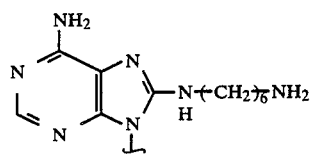

adenine base
(modified)

To the product oligonucleotide a variety of useful reporter groups ($R_5$,) may be attached. For example:

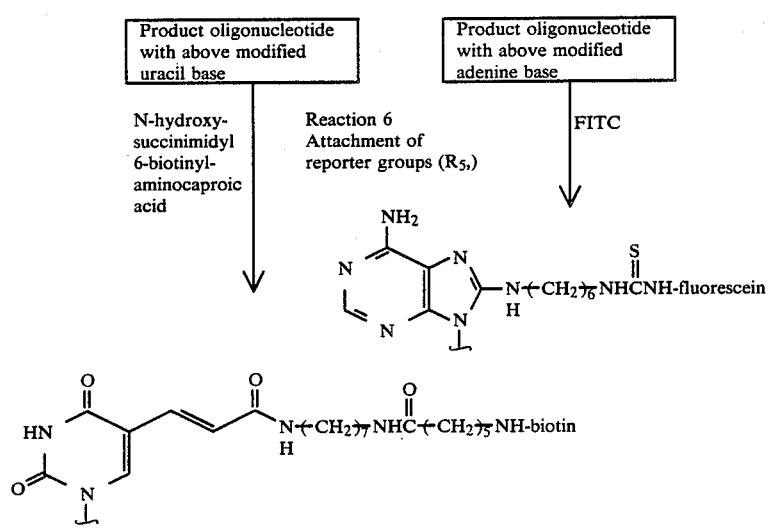

PRODUCT OLIGONUCLEOTIDES WITH REPORTER GROUPS (where $R_5$ = biotin or fluorescein)

Having discussed the process of the present invention in general terms and illustrated the same diagrammatically, each of the reactions referred to will now be discussed more specifically.

With reference to Reaction 1, masking of chemically reactive amines such as $N^4$ of cytosine, $N^6$ of adenine, $N^2$ of guanine, and alkyl or aryl amines of the modified bases with suitable masking groups can be conveniently accomplished in suitable solvents such as alcohols, pyridines, lutidines, chloroform, and the like, by reaction of the nucleosides with an excess of appropriate acid anhydrides for about 1 to 24 hours at temperatures in the range of 0° C. to 110° C., generally 20° C. to 80° C. Appropriate acid anydrides include acetic anhydride trifluoroacetic anhydride, benzoyl anydride, anisoyl anhydride, and the like. Preferred are acetyl, trifluoroacetyl, benzoyl, and isobutyryl anhydride.

Masking of the 5'-hydroxy in Reaction 2 can be conveniently effected by reaction of the nucleosides with a slight excess of appropriate acid-labile masking reagents, such as tritylchlorides, monomethoxytrityl chloride, dimethoxytrityl chloride (DMTCl), trimethoxytrityl chloride and the like. Preferred is dimethoxytrityl chloride. Typical reactions are carried out in suitable solvents, such as pyridine, lutidines, trialkylamines, and the like at temperatures in the range of $-20°$ C. to 120° C., generally 20° C. to 100° C., for about 1 to 48 hours. The preferred reaction utilizes 1.1 equivalents of DMTCl in pyridine at room temperature for 2 hours.

It is generally preferred that the respective products of each reaction described hereinabove be separated and/or isolated prior to use as a starting material for a subsequent reaction. Separation and isolation can be effected by any suitable purification procedure such as, for example, evaporation, filtration, crystallization, column chromatography, thin layer chromatography, etc. Specific illustrations of typical separation and isolation procedures can be had by reference to the appropriate examples described hereinbelow; however, other equivalent separation procedures can, of course, also be used. Also, it should be appreciated that, where typical reaction conditions (e.g., temperatures, mole ratios, reaction times) have been given, conditions both above and below the typical ranges can also be used, though generally less conveniently.

Activation to the phosphite analog illustrated in Reaction 3 can be most conveniently effected by treatment of the nucleoside compounds with suitable phosphitylating agents in appropriate solvents at temperatures in the range of $-90°$ C. to 60° C. for 1 minute to 2 hours. Suitable phosphitylating agents include methylphosphodichloridite, o-chlorophenylphosphodichloridite, p-chlorophenylphosphphosphodichloridite, methylphospho(dialkylamino) monochloridite, and the like. Appropriate solvents include pyridine, lutidines, acetonitrile, tetrahydrofuran, dioxane, chloroform and the like containing 0-20% appropriate base (generally 1-5 vol %) such as lutidines, collidines, triakylamines and the like. Preferred phosphitylating agents are methylphosphodichloridite, o-chlorophenylphosdichloridite, and methylphospho (di-iso-propylamino)-monochloridite. One example of such phosphytilating conditions are with 0.9 equivalents of methylphosphodichloridite in pyridine or acetonitrile containing 5% 2,6-lutidine for 5 to 10 minutes at room temperature or below.

The chemical incorporation of the modified nucleotide analog monomers into a growing nucleotide chain to produce a single strand oligonucleotide is illustrated in Reactions 4 and 4a. Typical condensations are in appropriate solvents at temperatures in the range of $-20°$ C. to 50° C., preferably at ambient temperature, for about 0.5 to 60 minutes. Appropriate solvent mixtures include pyridine, lutidines, acetonitrile, tetrahydrofuran, dioxane, chloroform and the like containing 0-20% appropriate base (generally 1 to 5 volume %) such as lutidines, collidines, trialkylamines and the like) for the chloridite method, or with a suitable activator such as 0-20% tetrazole for the amidite methods. The growing chain may be soluble, insoluble, or attached to a suitable solid support by appropriate chemical methods known in the art. Preferred is attachment to a solid support. Furthermore, the growing chain may or may not have previously incorporated one or more modified nucleotide analogs.

After condensation of the activated monomer to the growing chain, in Reaction 4, the initial product can be treated with suitable reagents to accomplish oxidation of the intermediate phosphite triester, optional capping to block unreacted 5'-hydroxyls on the oligonucleotide chain, and removal of the 5'-DMT group. Oxidation of the phosphite triester can be accomplished by treatment with 0.1-5 w/vol % iodine in suitable solvents, for example, tetrahydrofuran/water/lutidine mixtures. Chemical capping of unreacted 5'-hydroxyls can be accomplished by acetylation or acylation with, for example, acetic anhydride and 4- dimethylaminopyridine in tetrahydrofuran/lutidine mixtures. Removal of the 5'-blocking group, usually DMT, is most conveniently effected by treatment with mild organic acids in non-protic solvents, such as mild acids including, for example, 1-5 vol % dichloroacetic or trichloroacetic acid in chloroform or dichloromethane. The growing nucleotide chain, after removal of DMT, can now serve as acceptor for subsequent elongation by sequential reaction with activated monomers to eventually produce the oligonucleotide of desired length and sequence, as shown in Reaction 4a.

After an oligonucleotide of desired sequence is produced, Reaction 5 is accomplished to provide the product oligonucleotide. To this end, thiophenol treatment is used to remove methyl masking groups from phosphate triesters, and suitable aqueous alkali or ammonia treatment is used to remove other masking groups from the phosphate triester and benzoyl, acetyl, isobutyl, trifluoroacetyl, or other groups from the protected amines and/or to remove the product from the solid support. Removal of DMT from the oligonucleotide product is accomplished by the appropriate treatment with a mild acid, such as aqueous acetic acid at ambient temperature to 40° C. for 10 to 60 minutes. Such reactions may be accomplished before or during final purifications. Final purification is accomplished by appropriate methods, such as polyacrylamide gel electrophoresis, high pressure liquid chromatography (HPLC), reverse phase or anion exchange on DEAE cellulose, or combinations of these methods.

The process described herein for synthesis of oligonucleotides can utilize modified deoxyribonucleosides (where R' is H) or modified ribonucleosides (where R' is hydroxyl). When ribonucleosides are used, the 2'-hydroxyl is masked by an appropriate masking group such as, for example, that afforded by silylethers or tetrahydropyran. Other ribose analogs, including arabinose and 3'-deoxyribose, can also be accommodated in the process to produce the desired oligonucleotide.

The linker arm modifying a nucleotide base must be capable of binding one or more reporter groups or solid supports either prior to or after the chain extension coupling reaction. In the latter case, selected product oligonucleotides are reacted with suitable reagents to attach such reporter groups. For example, when modified bases are incorporated into the oligonucleotide and $R_2$ of the linker arm contains one or more primary amines, coupling with amine-reactive groups such as isocyanate, isothiocyanate, active carboxylic acid derivatives, epoxides or active aromatic compounds using suitable mild conditions is productive of amide, urea, thiourea, amine or aromatic amine linkages. For example, an oligonucleotide which contains an uracil or adenine base modified by a linker arm having a primary amine, as shown in the Reaction 5 diagram, can be reacted with a suitable reagent, such as fluorescein isothiocyanate (FITC) or N-hydroxysuccidimidyl 6-biotinylaminocaproic acid to provide a reporter group $R_5$ (fluorescein or biofin, respectively) bound to the linker arm as shown in Reaction 6. Other reporter groups which can be attached in similar manner include a wide variety of organic moieties such as fluoresceins, rhodamines, acridinium salts, dinitrophenyls, benzenesulfonyls, luminols, luciferins, carbohydrates and the like, or proteins capable of producing detectable products. Suitably active reporter groups are available commercially, or can be synthesized, for example, by processes of the type generally described in "Bioluminescence and Chemiluminescence" [M. DeLuca and W. McElroy, eds., Acad. Press, New York (1981)], by D. Roswell, et al., or H. Schroeder, et al. [*Meth. Enzymol.* LXII, 1978], and references cited therein.

Typically, attachment of reporter groups is conveniently accomplished in predominantly aqueous solvents by reaction of the substituent groups of modified bases wherein $R_2 = Cn_nH_{2n}NH_2$ with excess of the selected reporter group at temperatures in the range of about $-20°$ C. to $50°$ C. (preferably $20°$ C. to $40°$ C.) for 1 to 24 hours. Suitable solvents are an aqueous buffer and 0–50% organic solvents such as lower alcohols, tetrahydrofuran, dimethylformamide, pyridine, and the like. Preferred reporter group reactants include fluorescein, isothiocyanates, dinitrophenylisothiocyanates, fluorodinitrobenzene, N-hydroxysuccinimidylbiotin, N-hydroxysuccinimidyl dinitrobenzoate, isothiocyanates such as aminobutyl ethyl isoluminol isothiocyanate and the like, active esters of carboxyfluorescein, rhodamine, biotin adducts, dioxetanes, dioxamides, carboxyacridines, carbohydrates and the like, and suitably activated proteins.

Additionally, when the product oligonucleotide includes modified bases wherein R contains one or more carboxylic acids, mild condensations with, for example, primary alkylamines is productive of amide linkages. Typically, this is conveniently effected in predominantly acqueous solvents by reaction of the oligonucleotide with excess reporter group which contains a primary amine in the presence of suitable condensing agents, such as water-soluble carbodiimides, at temperatures in the range of about $-20°$ C. to $50°$ C. (preferably $20°$ C. to $40°$ C.) for 6 to 72 hours. Preferred reporter groups of this class include (amino-alkyl) -amino-napthalene-1, 2-dicarboxylic acid hydrazides, amino-fluoresceins, aminorhodamines, aminoalkyl luminols, aminoalkylaminobenzenesulfonyl adducts, amino sugars, aminoproteins, and the like. Furthermore, the chemical synthesis of the initial oligonucleotide product may be accomplished with modified nucleotide monomers wherein prior to the coupling reaction, such reporter groups are attached to the linker arm. If any such reporter groups would adversely affect the coupling reaction they are appropriately blocked to forestall any such adverse effect. On the other hand, certain other reporter groups are substantially unreactive with respect to the coupling reaction and therefore do not require blocking. For example, nitrophenyl adducts may be attached to the substituent group prior to the coupling reaction, and without masking, may be present on the modified nucleotide monomer during the coupling reaction without adverse effect.

Reporter groups useful in the method of this invention generally include aromatic, polyaromatic, cyclic, and polycyclic organic moieties which are further functionalized by inclusion of heteroatoms such as nitrogen, oxygen, sulfur and the like, or proteins capable of producing an appropriately detectable product.

Product oligonucleotides can include more than one type of modification or more than one modified base. An illustrative example of an oligonucleotide of this type is one of the structure:

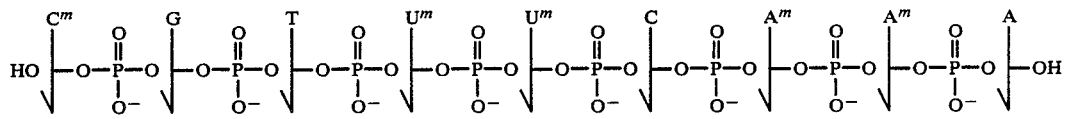

wherein $C^m$ is 5-(3-aminopropyl) cytosine, $U^m$ is 5-[N-(4-aminobutyl)-1-acrylamido]uracil, and $A^m$ is 8-[6-2,4-dinitrophenyl)-aminohexyl] minoadenine. This product is further modified by reaction with fluorescein isothiocyanate to provide a fluorescein reporter qroup on $C^m$ and $U^m$.

Such a product oligonucleotide illustrates the variety of the selection of modified and unmodified nucleotide units in a product oligonucleotide made possible by the process of the present invention. More specifically, such oligonucleotide illustrates the use of more than one type of nucleotide unit having its base modified by a linker arm to which is bound a reporter group whose function may be the same or different from those of reporter groups bound to the substituent group of other similarly modified nucleotide units thereof. Also illustrated are units whose bases are modified by linker arm to which reporter groups are bound after the coupling reaction, i.e., $C^m$ and $U^m$, whereas $A^m$ is illustrative of a unit whose base is modified by a linker arm to which a dinitrophenyl reporter group was attached prior to the coupling reaction. Such oligonucleotide additionally illustrates that it can include more than one nucleotide unit of the same type, and that it can include units having unmodified bases intermixed with units having modified bases.

Instead of attaching reporter groups to the primary amines of the linker arm as illustrated in Reaction 6, such amine or other group can alternatively be coupled to suitably activated solid supports. This produces a single strand oligonucleotide which is covalently bound to such supports through the modified bases. Such solid supports are useful in the detection and isolation of complementary nucleic acid components. Alternatively, the modified nucleoside monomers can be coupled to solid supports prior to the chain extension coupling Reaction 4, to thereby provide solid supports for such monomers during the coupling reaction.

The following specific examples are provided to enable those skilled in the art to practice the invention. The examples should not be considered limitations upon the scope of the invention, but merely as being illustrative and representative thereof. To aid in structural clarification, references are made to the reactions illustrated in the aforementioned process diagram.

EXAMPLE I

This example illustrates the synthesis of a modified nucleoside precursor 5-(3-trifluoracetylaminopropenyl)-2'-deoxyuridine.

5-Chloromercuri-2'-deoxyuridine (3.6 g, 7.8 mmol) is suspended in 200 ml methanol. N-Allyltrifluoroacetamide (6.8 ml, 55 mmol) is added, followed by addition of 41 ml of 0.2N lithium tetrachloropalladate in methanol. After 18 hours stirring at room temperature, the reaction is gravity filtered to remove the black solid palladium, and the yellow methanolic filtrate is treated with five 200 mg portions of sodium borohydride, then concentrated under reduced pressure to solid residue. The residue is purified by flash column chromatography on silica gel eluting 15 vol % methanol in chloroform. Appropriately pure fractions of product are combined and concentrated under reduced pressure to give crystalline 5-(3-trifluoroacetylamino-propenyl)-2'-deoxyuridine (2.4 g). UV $\lambda_{max}$ 291 nm ($\gamma$ 7800), $\lambda$ min 266 nm, ($\gamma$ 4400); TLC (Silica eluting 150 vol % methanol in chlorofrom) $R_f=0.4.1$

EXAMPLE II

This example illustrates the synthesis of a modified nucleoside precursor 5-[N-(trifluoroacetylaminoheptyl)-1-acrylamido]-2'-deoxyuridine.

5-Chloromercuri-2'-deoxyuridine (3.6 g, 7.8 mmol) is suspended in 200 ml methanol. N-(7-trifluoroacetylamino-heptyl)-acrylamide (55 mmol) is added, followed by addition of 41 ml of 0.2N lithium tetrachloropalladate in methanol. After 18 hours stirring at room temperature, the reaction is gravity filtered to remove the black solid palladium, and the yellow methanolic filtrate is treated with five 200 mg portions of sodium borohydride, then concentrated under reduced pressure to solid residue. The residue is purified by flash column chromatography on silica gel eluting 10 vol % methanol in chloroform. Appropriately pure fractions of product are combined and concentrated under reduced pressure to give crystalline 5-[N-(7-trifluoroacetylaminoheptyl)-1acrylamido]-2'-deoxyuridine (2.8 g). UV $\lambda_{max}$ 302 nm ($\epsilon$ 18000), $\lambda_{min}$ 230 nm, 280 nm; TLC (silica eluting 15 vol % methanol in chloroform) Rf=0.3.

EXAMPLE III

This example illustrates masking of 5'-hydroxyl to produce 5'-dimethoxytrityl-5-(3-trifluoroacetylaminopropenyl)-2'-deoxyuridine as illustrated in Reaction 2.
5-(3-trifluoroacetylaminopropenyl)-2'-deoxyuridine (2.4 g) is thoroughly evaporated twice from pyridine, then stirred in 40 ml pyridine. Dimethoxytrityl(DMT)-chloride (2.3 g, 6.6 mmol) is added, and the mixture stirred at room temperature for four hours. After thin layer chromatography (TLC) on silica eluting 10 vol % methanol in chloroform indicates reaction is complete, the reaction is concentrated to a solid residue. This residue is purified by column chromatography on silica eluting chloroform until all faster running impurities have eluted, then bringing off product with 5 vol % methanol in chloroform. The residue is then concentrated to give 5'-dimethoxytrityl-5-(3-trifluoroacetylaminopropen-1-yl)-2'1-deoxyuridine as a white fluffy solid (4 g). Product decomposes upon heating UV $\lambda_{max}$ 291 nm, $\lambda_{min}$ 266 nm; TLC $R_f$ 0.6 on silica eluting 10 vol % methanol in chloroform.

EXAMPLE IV

This example illustrates hydrogenation of exocyclic double bond and 5'-hydroxyl masking to produce 5'-dimethoxytrityl-5-(3-trifluoroacetylaminopropyl)-2'-deoxyuridine.

Repeating the nucleoside precursor synthesis and 5'-hydroxyl masking procedures of Examples I and III, but, prior to the addition of the DMT chloride, subjecting the purified 5-(3-trifluoroacetylaminopropenyl)-2'-deoxyuridine to two atmospheres of hydrogen while stirring at room temperature in methanol over 10% palladium-on-carbon catalyst is productive of 5'-dimethoxytrityl-5-(3-trifluoroacetylaminopropyl)-2'-deoxyuridine.

Examples V to VII illustrate the synthesis of additional modified uracil nucleosides, and subsequent masking of 5'-hydroxyls as represented by Reaction 2.

EXAMPLE V

Repeating the nucleoside precursor synthesis and 5' hydroxyl masking procedures of Examples I and III, but replacing N-allyltrifluoroacetamide with compounds numbered 1 through 8 below is productive of the compounds numbers 1' through 8' below, respectively; i.e., substitution of 1: N-(3-butenyl)trichloroacetamide
2: N-(5-hexenyl)trifluoroacetamide
3: N-(2-methyl-2-propenyl)trifluoroacetamide
4: N-(4-ethenylphenylmethyl)trifluoroacetamide
5: N-(1-methyl-3-butenyl)trifluoroacetamide
6: N-(12-trichloroaminododecyl)acrylamide
7: N-(pertrifluoroacetylpolylysyl)acrylamide
8: N-(3-trifluoroacetylamidopropyl)acrylamide
is productive of
1': 5'-dimethoxytrityl-5-(4-trichloroacetylaminobuten-1-yl)-2'-deoxyuridine
2': 5'-dimethoxytrityl-5-(6-trifluoroacetylaminohexen-1-yl)-2'-deoxyuridine
3': 5'-dimethoxytrityl-5-(3-trifluoroacetylamino-2-methylpropen-1-yl)-2'-deoxyuridine
4': 5'-dimethoxytrityl-5-[2-(4-trifluoroacetylaminomethylphenyl)ethen-1-yl]-2'-deoxyuridine
5': 5'-dimethoxytrityl-5-(4-trifluoroacetylamino-4-methylbuten-1-yl)-2'-deoxyuridine
6': 5'-dimethoxytrityl-5-[N-(12-trichloroacetylaminododecyl)-1-acrylamido]-2'-deoxyuridine
7': 5'-dimethoxytrityl-5-[N-(pertrifluoroacetylpolylysyl)-1-acrylamido]-2'-deoxyuridine
8': 5'-dimethoxytrityl-5-[N-(3-trichloroacetylaminopropyl)-acrylamido]-2'-deoxyuridine

EXAMPLE VI

Repeating the 5'-hydroxyl masking procedure of Example III but replacing 5-(3-trifluoroacetylaminopropenyl)-2'-deoxyuridine with the 5-substituted-2'-deoxyuridines numbered 9 through 18 below is productive of the products numbered 9' through 18' below, respectively; i.e. substituting
9: 5-(propen-1-yl)-2'-deoxyuridine
10: 5-(carbmethoxyethyl)-2'-deoxyuridine 11: 5-(3-carbmethoxyprop-1-yl)-2'-deoxyuridine
12: 5-(4-carbmethoxy-2-methylbuten-1-yl)-2'-deoxyuridine
13: 5-(3-cyanopropen-1-yl)-2'-deoxyuridine
14: 5-(4-cyano-2-methylbuten-1-yl)-2'-deoxyuridine
15: 5-[2-(4-carbmethoxyphenyl)ethen-1-yl]-2'-deoxyuridine
16: 5-(4-acetoxybuten-1-yl)-2'-deoxyuridine
17: 5-(4-acetoxybut-1-yl)-2'-deoxyuridine
18: 5-[4-(2,4-dinitrophenyl)butyl]-2'-deoxyuridine
is productive of the following 5'-dimethoxytrityl-5 alkyl-2'-deoxyuridines
9': 5'-dimethoxytrityl-5-(propen-1-yl)-2'-deoxyuridine
10': 5'-dimethoxytrityl-5-(2-carbmethoxyethyl)-2'-deoxyuridine
11': 5'-dimethoxytrityl-5-(3-carbmethoxyprop-1-yl)-2'-deoxyuridine
12': 5'-dimethoxytrityl-5-(4-carbmethoxy-2-methylbuten-1-yl)-2'-deoxyuridine
13': 5'-dimethoxytrityl-5-(3-cyanopropen-1-yl)-2'-deoxyuridine
14': 5'-dimethoxytrityl-5-(4-cyano-2-methylbuten-1-yl)-2'-deoxyuridine
15': 5'-dimethoxytrityl-5-[2-(4-carbmethoxyphenyl)ethen-1-yl]-2'-deoxyuridine
16': 5'-dimethoxytrityl-5-(4-acetoxybuten-1-yl)-2'-deoxyuridine
17': 5'-dimethoxytrityl-5-(4-acetoxybut-1-yl)-2'-deoxyuridine
18': 5'-dimethoxytrityl-5-[4-(2,4-dinitrophenyl)butyl]-2'-deoxyuridine

EXAMPLE VII

Repeating the nucleoside precursor synthesis and 5'-hydroxyl masking procedures of Examples I–VI, but replacing 5-chloromercuri-2'-deoxyuridine with 5-chloromercuriuridine is productive of the corresponding 5'-dimethoxytrityl-5-substituted uridines.

Examples VIII to XI illustrate the synthesis of modified cytosine nucleosides. Since cytosine nucleosides, as well as adenosine nucleosides, have reactive groups in their bases unlike the uracil nucleosides, such reactive groups are masked to prevent unwanted reactions therewith. These examples illustrate masking of reactive groups on the cytosine base moiety as in Reaction 1, as well as masking of the 5'-hydroxyl as in Reaction 2.

EXAMPLE VIII 5-(3-trifluoroacetylaminopropenyl)-$N^4$-benzoyl-2'-deoxycytidine Repeating the nucleoside precursor synthesis procedure of Example I, but replacing 5-chloromercuri-2'-deoxyuridine with 5-chloromercuri-2'-deoxycytidine is productive of 5-(3-trifluoroacetylaminopropenyl)-2'-deoxycytidine (UV max 287 mn). Purified 5-(3-trifluoroacetyl-aminopropenyl)-2'-deoxycytidine (1.3 g, 4.6 mmol) is stirred in 80 ml anhydrous ethanol, benzoyl anhydride (1.5 g, 7 mmol) is added, and the reaction refluxed. Five additional 1.5 g portions of benzoyl anhydride are added hourly. After the reaction is judged complete by thin layer chromatography [silica plates eluting n-butanol/methanol/conc NH$_4$OH/H$_2$O (60:20:1:20)in 6–10 hours, the reaction is cooled and concentrated under reduced pressure to a semisolid. The solid is triturated with ether three times, decanted and dried. The crude product is crystallized from water to give chromatographically pure $N^4$-benzoyl-5-(3-trifluoroacetylaminopropenyl)-2'-deoxycytidine as a white solid. The product decomposes above 120° C.; UV $\lambda_{max}$311 nm.

EXAMPLE IX

5'-Dimethoxytrityl-5-(3-trifluoroacetylaminopropenyl)-$N^4$-benzoyl-2'-deoxycytidine Repeating the 5'-hydroxyl masking procedure of Example III, but replacing 5-(3-trifluoroacetylaminopropenyl)-2'-deoxyuridine with 5-(3-trifluoroacetyleaminopropenyl)-$N^4$-benzoyl-2'-deoxycytidine is productive of 5'-dimethoxytrityl-5-(3-trifluoroacetylaminopropenyl)-$N^4$-benzoyl-2'-deoxycytidine.

EXAMPLE X

Repeating the nucleoside precursor synthesis and 5'hydroxyl masking procedures of Examples VIII and IX, but replacing N-allyltrifluoroacetamide with the respective N-alkyltrifluoroacetamides of Example V is productive of the corresponding 5'-dimethoxytrityl-5-(trifluoroacetylaminoalkyl)-$N^4$-benzoyl-2'-deoxycytidines numbered 1″ through 8″ below.
1″: 5'-dimethoxytrityl-5-(4-trifluoroacetylaminobuten-1-yl)-$N^4$-benzoyl-2'-deoxycytidine
2″: 5'-dimethoxytrityl-5-(6-trifluoroacetylaminohexen-1-yl)- $N^4$-benzoyl-2'-deoxycytidine
3″: 5'-dimethoxytrityl-5-(3-trifluoroacetylamino-2-methylpropen-1-yl)-$N^4$-benzoyl-2'-deoxycytidine
4″: 5'-dimethoxytrityl-5-[2-(4trifluoroacetylaminomethylphenyl)ethen-1-yl]-$N^4$-benzoyl-2'-deoxycytidine
5″: 5'-dimethoxytrityl-5-(4-trifluoroacetylamino-4-methylbuten-1-yl)-$N^4$-benzoyl-2'-deoxycytidine
6″: 5'-dimethoxytrityl-5-[N-(12-trifluoroacetylaminododecyl)-1acrylamido]-$N^4$-benzoyl-2'-deoxycytidine
7″: 5'-dimethoxytrityl-5-[N-(pertrifluoroacetyl-polylysyl)-1-acrylamido]-$N^4$-benzoyl-2'-deoxycytidine
8″: 5'-dimethoxytrityl-5-[N-(3-trifluoroacetylaminopropyl)-1-acrylamido]-$N^4$-benzoyl-2'-deoxycytidine

EXAMPLE XI

Synthesis of 5'-dimethoxytrityl-$N^4$-benzoyl-5-(2-carbmethoxyethenyl)-2'-deoxycytidine 5-(2-Carbmethoxyethenyl)-2'-deoxycytidine (0.82 g, 2.6 mmol) is stirred in 50 ml anhydrous ethanol. Benzoic anhydride (500 mg, 2.2 mmol) is added, and the reaction heated to reflux. Five additional 500 mg portions of benzoic anhydride are added hourly. After the reaction is judged complete by thin layer chromatography (usually 6–8 hours) the reaction is cooled, and evaporated under reduced pressure to a yellow semi-solid. Chromatography on silica gel eluting a linear 1:19 to 1:3 methanol/chloroform mixture followed by thorough evaporation of appropriately combined fractions gives $N^4$-benzoyl-5-(2-carbmethoxyethenyl)-2'-deoxycytidine as an amorphous white solid. UV $\lambda_{max}$ 296 nm, $\lambda_{min}$ 270 nm. The solid is dried thoroughly, and dissolved in 20 ml pyridine. Dimethoxytrityl chloride (1.1 eq) is added, and the reaction stirred at ambient temperature for six hours. Concentration to a solid followed by column chromatography on silica gel eluting 10% methanol in chloroform yields 5'-dimethoxytrityl-N⁴-benzoyl-5-(2-carbmethoxye-thenyl)-2'-deoxycytidine as a fluffy off-white solid.

EXAMPLE XII

Repeating the nucleoside precursor synthesis procedure of Example XI, but replacing 5-(2-carbmethoxy-hetenyl)-2'-deoxycytidine with the following compounds numbered 19 through 27 below is productive of the corresponding compounds numbered 19' through 27° below, respectively, i.e., substituting:
19: 5-(2-carbmethoxyethyl)-2'-deoxycytidine
20: 5-(3-carbmethoxyprop-1-yl)-2'-deoxycytidine
21: 5-(4-carbmethoxy-2-methylbuten-1-yl)-2'-deoxycytidine
22: 5-(3-cyanopropen-1-yl)-2'-deoxycytidine
23: 5-(4-cyano-2-methylbuten-1-yl)-2'-deoxycytidine
24: 5-[2-(4-carbmethoxyphenyl)ethen-1-yl]-2'-deoxycytidine
25: 5-(4-acetoxybuten-1-yl)-2'-deoxycytidine
26: 5-(4-acetoxybut-1-yl)-2'-deoxycytidine
27: 5-[4-(2,4-dinitrophenyl)butyl]-2'-deoxycytidine
is productive of the following 5'-dimethoxytrityl-N⁴-benzoyl-5-alkyl-2'-deoxycytidines:
19': 5'-DMT-N⁴-benzoyl-5-(2-carbmethoxyethen-1-yl)-2'-deoxycytidine
20': 5'-DMT-N⁴-benzoyl-5-(3-carbmethoxyprop-1-yl)-2'-deoxycytidine
21': 5'-DMT-N⁴-benzoyl-5-(4-carmethoxy-2-methylbuten-1-yl)-2'-deoxycytidine
22': 5'-DMT-N⁴-benzoyl-5-(3-cyanopropen-1-yl)-2'-deoxycytidine
23': 5'-DMT-N⁴-benzoyl-5-(4-cyano-2-methylbuten-1-yl)-2'-deoxycytidine
24': 5'-DMT-N⁴-benzoyl-5-[2-(4-carbmethoxyphenyl)ethen-1-yl]-2'-deoxycytidine
25': 5'-DMT-N⁴-benzoyl-5-(4-acetoxybuten-1-yl)-2'-deoxycytidine
26': 5'-DMT-N⁴-benzoyl-5-(4-acetoxybut-1-yl)-2'-deoxycytidine
27': 5'-DMT-N⁴-benzoyl-5-[4-(2,4-dinitrophenyl)butyl]-2'-deoxycytidine Similarly, the use of the other acid anhydrides, e.g., acetic anhydride, anisoyl anhydride, or tolyl anhydride, is productive of the corresponding N⁴-acyl or N⁴-acetyl 5-alkyl-2'-deoxycytidines of Examples X and XI wherein benzoyl is replaced by acetyl or acyl.

EXAMPLE XIII

Repeating the nucleoside precursor synthesis and 5'-hydroxyl masking procedures of Examples VIII to X, but replacing 5-chloromercuri-2'-deoxycytidine with 5-chloromercuricytidine is productive of the corresponding 5'-dimethoxytrityl-N⁴-benzoyl-5-substituted cytidines.

EXAMPLE XIV

This example typifies the masking of reactive base moieties and the masking of 5'-hydroxyl of adenine nucleosides.

N⁶-benzoyl-8-(6-aminohexyl)amino-2'-deoxyadenosine (4 mmol) is stirred in 60 ml anhydrous ethanol. Trifluoroacetic anhydride (6 mmol) is added, and the reaction stirred at room temperature. Two additional portions of trifluoroacetic anhydride are added hourly. After four hours, the reaction is concentrated to a solid residue, and lyophilized overnight. The crude N⁶-benzoyl-8-(6-trifluoroacetylaminohexyl)amino-2'-deoxyadenosine is dried thoroughly and concentrated to a solid residue twice from pyridine. The solid is stirred in 40 ml of pyridine, and dimethoxytrityl chloride (6.5 mmol) is added. After four hours, the reaction is concentrated to leave a solid residue. Purification by column chromatography on silica gel eluting a multi-step gradient of 0 to 15% methanol in chloroform gives 5'-dimethoxytrityl-N⁶-benzoyl-8-(6-trifluoroacetylaminohexyl)amino-2'-deoxyadenosine as an off-white solid.

Examples XV and XVII typify the activation of 5'-masked 5-substituted, and naturally occurring nucleosides, to their respective phosphomonochloridites, as illustrated in Reaction 3 of the diagram.

EXAMPLE XV

Preparation of 3'-phosphomonochloridite of 5'-DMT-5-(3-trifluoroacetylaminoprop-1-yl)-2'-deoxyuridine Dry 5'-DMT-5-(3-trifluoroacetylaminoprop-1-yl)-2'-deoxyuridine (1.54 g, 2.2 mmol) is lyophilized from 20 ml benzene three times for more than twelve hours each to remove residual water and solvents. The resulting very fluffy white powder is transferred to a nitrogen atmosphere while still under vacuum and dissolved in anhydrous acetonitrile containing 5 vol % 2,6-lutidine to a final nucleoside concentration of 30 mM. While swirling vigorously under nitrogen, one rapid bolus of methylphosphodichloridite (1.0 eq) is added by syringe. The reaction is swirled for about one minute under nitrogen. The resulting crude 5'-DMT-5-(3-trifluoroacetylaminoprop-1-yl)-2'-deoxyuridine 3'-methylphosphomonochloridite reaction solution is then used directly for deoxyoligonucleotide synthesis (Example XVIII) with no further purification, [³¹P-NMR(CH₃CN/CDCl₃) generally indicates 40–70 mol % desired product (167.5 ppm); remainder is composed of bis-3',3'-[5'DMT-5-(3-trifluoroacetylaminoprop-1-yl)-2'-deoxyuridylyl]methylphosphite (140 ppm) and 5'-DMT-5-(3-trifluoroacetylaminoprop-1-yl)-2'-deoxyuridine 3'-methylphosphonate (9.5 ppm), the latter product being formed in amounts reflecting the presence of water in the reaction.]

EXAMPLE XVI

Preparation of 3'-phosphomonochloridites of the naturally occurring 2'-deoxynucleosides Repeating the procedure of Example XV, but replacing 5'-DMT-5-(3-trifluroacetylaminoprop-1-yl)-2'-deoxyuridine with:
5'-DMT thymidine
5'-DMT-N⁴-benzoyl-2'-deoxycytidine
5'-DMT-N⁶-benzoyl-2'-deoxyadenosine
5'-DMT-N²-isobutyryl-2'-deoxyguanosine
is productive of the corresponding phosphomonochloridites, viz.:
5'-DMT thymidine 3'-methylphosphomonochloridite
5'-DMT-N⁴-benzoyl-2'-deoxycytidine 3'-methylphosphomonochloridite
5'-DMT-N⁶-benzoyl-2'-deoxyadenosine 3'-methylphosphomonochloridite
5'-DMT-N²-isobutyryl-2'-deoxyguanosine 3'-methylphosphomonochloridite

EXAMPLE XVII

Repeating the phosphomonochloridite synthesis procedures of Examples XV and XVI, but replacing methylphosphodichloridite with o-chlorophenylphosphodichloridite is productive of the corresponding 5'-DMT-nucleoside 3'-phosphomonochloridites, viz.:

5'-DMT-5-(3-trifluoroacetylaminopropyl)-2'-deoxyuridine 3'-o-chlorophenylphosphomonochloridite 5'-DMT thymidine 3'-o-chlorophenylphosphomonochloridite 5'-DMT-N⁴-benzoyl-2'-deoxycytidine 3'-o-chlorophenylphosphomonochloridite 5'-DMT-N⁶-benzoyl-2'-deoxyadenosine 3'-o-chlorophenylphosphomonochloridite 5'-DMT-N²-isobutyryl-2'-deoxyguanosine 3'-o-chlorophenylphosphomonochloridite Similarly, the use of p-chlorophenylphosphodichloridite is productive of the analogous 3'-p-chlorophenylphosphomonochloridite adducts. [³²P]NMR (CH₃CN/CDCl₃) of o-chlorophenylphosphomonochloridite products 160.7, 160.5 ppm (diasteriomers).

Examples XVIII–XXIV typify the chemical synthesis of oligonucleotides which incorporate modified bases, as illustrated by Reactions 4 and 5 in the diagram.

EXAMPLE XVIII

Synthesis of deoxyoligonucleotides containing 5-(3-aminopropyl)-uracil and naturally occurring nucleotide units The phosphomonochloridite synthesis procedures of Examples XV and XVI are accomplished immediately before deoxyoligonucleotide synthesis, and the resulting products are used directly as 30 mM crude 3'-methylphosphomonochloridites in anhydrous acetonitrile/5 vol % 2,6-lutidine.

Solid support (5-DMT-N⁶-benzoyl-2'-deoxyadenosine 3'-succinamidepropyl silica, 250 mg, 20 μeq) is put into a suitable reaction flow vessel (glass or Teflon ® column or funnel). The solid support is preconditioned by successive treatments with acetonitrile/5 vol % lutidine, 2 w/v % iodine in tetrahydrofuran/water/lutidine for 2 minutes, acetonitrile/5% lutidine, chloroform, 4 vol % dichloroacetic acid in chloroform for 2.5 minutes, and acetonitrile/5% lutidine, where treatments are total volumes of 5–15 ml in either 2 or 3 portions or by constant flow, as desired.

The deoxyoligonucleotide is synthesized in accordance with Reaction 4 by sequential addition of the desired activated 5'-DMT-nucleoside 3'-methylphosphomonochloridite monomer and coupling thereof to the free 5'-hydroxyl of the terminal unit of the growing nucleotide chain, which unit is initially the only unit of the chain, i.e., the deoxyadenosine based unit comprising the solid support. Additions are by reaction of 10 ml of the crude 30 mM monochloridites chosen from Examples XV and XVI with the now unprotected 5'-hydroxyl of the chain in either 2 or 3 portions or by constant flow, for 2 to 6 minutes. The first phosphomonochloridite addition followed by one complete reagent cycle consists of sequential treatments with:

5'-DMT-5-(3-trifluoroacetylaminopropyl)-2'-deoxyuridine 3'-methylphosphomonochloridite acetonitrile/lutidine wash capping for 5 minutes with 0.3 M 4-dimethylaminopyridine in acetic anhydride/lutidine/tetrahydrofuran (1:3:2)

acetonitrile/5% lutidine wash oxidation with 2% iodine in tetrahydrofuran/water/lutidine (6:2:1) for 2 minutes acetonitrile/5% lutidine wash chloroform wash removal of DMT by 2.5 minute treatment with 4 vol % dichloroacetic acid in chloroform chloroform wash acetonitrile/lutidine wash The above cycle is repeated thirteen times, each time replacing 5'-DMT-5-(3-trifluoroacetylaminopropyl)-2'-deoxyuridine 3'-methylphosphomonochloridite with a different one of the following 3'-methylphosphomonochloridites:

5'-DMT thymidine 3'-methylphosphomonochloridite

5'-DMT-5-(3-trifluoroacetylaminopropyl)-2'-deoxyuridine 3'-methylphosphomonochloridite 5'-DMT-N⁶-benzoyl-2'-deoxyadenosine 3'-methylphosphomonochloridite 5'-DMT-N⁴-benzoyl-2'-deoxycytidine 3'-methylphosphomonochloridite 5'-DMT-N²-isobutyryl-2'-deoxyguanosine 3'-methylphosphomonochloridite 5'-DMT-5-(3-trifluoroacetylaminopropyl)-2'-deoxyuridine 3'-methylphosphomonochloridite 5'-DMT thymidine 3'-methylphosphomonochloridite 5'-DMT-5-(3-trifluoroacetylaminopropyl)-2'-deoxyuridine 3'-methylphosphomonochloridite 5'-DMT thymidine 3'-methylphosphomonochloridite 5'-DMT-5-(3-trifluoroacetylaminopropyl)-2'-deoxyuridine 3'-methylphosphomonochloridite 5'-DMT-N²-isobutyryl-2'-deoxyguanosine 3'-methylphosphomonochloridite 5'-DMT-N⁶-benzoyl-2'-deoxyadenosine 3'-methylphosphomonochloridite 5'-DMT-N⁴-benzoyl-2'-deoxycytidine 3'-methylphosphomonochloridite in respective order, deleting dichloroacetic acid treatment during the last reagent cycle. The support is transferred and treated with 2 ml concentrated ammonium hydroxide for 4 hours at ambient temperature to release the product from the support. The supernatant is removed, the solid washed three times with 0.5 ml concentrated ammonium hydroxide, and the combined supernatants are sealed and heated at 50° C. overnight. The clear yellow supernatant is lyophilized thoroughly. Initial purification is accomplished by reverse phase high pressure liquid chromatography (HPLC) on an RP-8 (C-8) column eluting a 60 minute linear gradient of 0 to 30% vol % acetonitrile in 25 mM ammonium acetate, pH 6.8. The 5'-DMT-terminated product, eluting as a sharp peak at about 40 minutes, is collected; all shorter chains, both capped and uncapped, elute before 25 minutes. The collected product is evaporated to a solid residue, treated with 80% acetic acid at ambient temperature for 20 minutes (to remove DMT), lyophilized to a solid residue, and dissolved in a small amount of aqueous buffer. The product, generally greater than 90% homogeneous after HPLC, is further purified by conventional electrophoresis on 20% polyacrylamide gels (1 to 6 mm thick) by excision and extraction of the appropriate product band (product generally migrates slower than unmodified deoxyligonucleodites of similar length). The purified 5-aminopropyl-uracil-containing pentadecadeoxyoligonucleotide product illustrated diagrammatically below, wherein $U^m$=5-(3 aminopropyl)uracil, is thereby produced.

36: 5'-dimethoxytrityl-5-[2-(4-trichloroacetylaminomethylphenyl)ethen-1-yl]-2'-deoxyuridine
37: 5'-dimethoxytrityl-5-[N-(pertrifluoroacetyl-

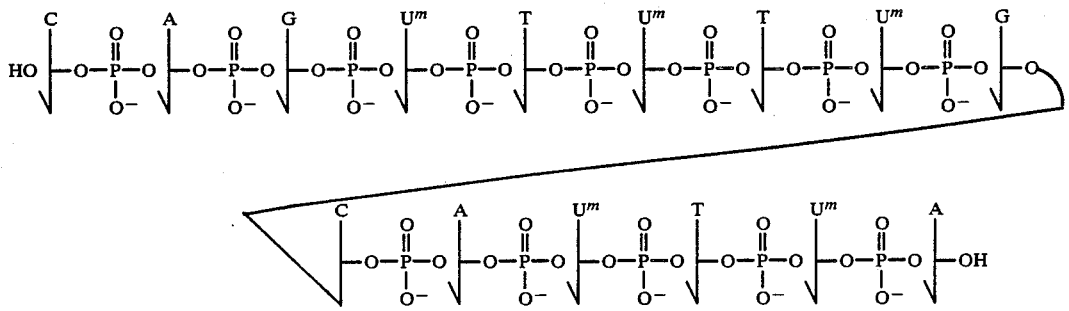

Note the conventional deprotection of the oligonucleotide with ammonia has also removed the trifluoroacetyl masking group on the substituent.

The length and sequence of this oligonucleotide may then be determined by $^{32}$P-kinasing and sequencing using suitable protocols, for example the protocols heretofore used to determine the length and sequence of the prior art oligonucleotides in which the bases of the nucleotide units therein are unmodified.

Similarly, intentional variation of the order and number of methylphosphomonochloridite additions employed here is productive of other 5-(modified)uracil-containing deoxyoligonucleotides which vary in selected length and base sequence. In addition, replacement of the nucleoside 3'-methylphosphomonchloridite adducts of Examples XV and XVI with the corresponding 3'-o- or p-chloro-phenylphosphomonochloridite adducts of Example XVII and inclusion of pyridinium oximate treatment to remove chlorophenyl blocking groups (at the end of the deoxyoligonucleotide synthesis and before concentrated ammonium hydroxide treatment) is productive of the same deoxyoligonucleotide products.

EXAMPLE XIX

Repeating the phosphomonochloridite and deoxyoligonucleotide synthesis procedures of Examples XV to XVIII, but replacing 5'-DMT-5-(3-trifluoroacetylaminopropyl)-2'-deoxyuridine with the 5'-DMT-5alkyl-2'-deoxy-uridines numbered 28 through 38 below is productive of the corresponding oligonucleotides having uracil bases $U^m$ numbered 28' through 38' below, respectively, i.e., substituting:

28: 5'-dimethoxytrityl-5-(3-trifluoroacetylaminopropen-1-yl)-deoxyuridine
29: 5'-dimethoxytrityl-5-(4-trifluoroacetylaminobut-1-yl)-2'-deoxyuridine
30: 5'-dimethoxytrityl-5-(4-trifluoroacetylaminobuten-1-yl)-2'-deoxyuridine
31: 5'-dimethoxytrityl-5-(6-trifluoroacetylaminohex-1-yl)-2'-deoxyuridine
32: 5'-dimethoxytrityl-5-(6-trifluoroacetylaminohexen-1-yl)-2'-deoxyuridine
33: 5'-dimethoxytrityl-5-(2-trifluoroacetylaminoprop-2-yl)-2'-deoxyuridine
34: 5'-dimethoxytrityl-5-(3-trifluoroacetylamino-2-methyl-propen-1-yl)-2'-deoxyuridine
35: 5'-dimethoxytrityl-5-(3-trifluoroacetylamino-2-methyl-propan-1-yl)-2'-deoxyuridine
polylysyl)-1-acrylamido]-2'-deoxyuridine
38: 5'-DMT-5-[N-(7-trifluoro-acetylaminoheptyl)-1acrylamido]-2'-deoxyuridine
is productive of the deoxynucleotides corresponding to the product of Example XVIII, wherein $U^m$ is:
28': 5-(3-aminopropen-1-yl) uracil
29': 5-(4-aminobut-1-yl) uracil
30': 5-(4-aminobuten-1-yl) uracil
31': 5-(6-aminohex-1-yl) uracil
32': 5-(6-aminohexen-1-yl) uracil
33': 5-(3-aminoprop-2-yl) uracil
34': 5-(3-amino-2-methylpropen-1-yl) uracil
35': 5-(3-amino-2-methylprop-1-yl) uracil
36': 5-[2-(4-aminoethylphenyl)ethen-1-yl] uracil
37': 5-[N-(polylysyl)-1-acrylamido] uracil
38': 5-[N-(7-aminoheptyl)-1-acrylamido] uracil
Similarly, by employing other 5'-DMT-5-(acylaminoalkyl)-2'-deoxyuridines, the analogous deoxyoligonucleotides are produced.

EXAMPLE XX

Repeating the phosphomonochloridite and deoxyoligonucleotide synthesis procedures of Examples XV to XVIII, but replacing 5'-DMT-5-(3-trifluoroacetylaminopropyl)-2'-deoxyuridine with 5-substituted -2'-deoxyuridines numbered 37a through 46 below is productive of the corresponding oligonucleotides having the $U^m$ uracil bases numbered 37a' through 46' below respectively; i.e., substituting:

37a: 5'-DMT-5-(propen-1-yl)-2'-deoxyuridine
38a: 5'-DMT-5-(2-carbmethoxyethyl)-2'-deoxyuridine
39: 5'-DMT-5-(3-carbmethoxyprop-1-yl)-2'-deoxyuridine
40: 5'-DMT-5-(4-carbmethoxy-2-methylbuten-1-yl)-2'-deoxyuridine
41: 5'-DMT-5-(3-cyanopropen-1-yl)-2'-deoxyuridine
42: 5'-DMT-5-(4-cyano-2-methylbuten-1-yl)-2'-deoxyuridine
43: 5'-DMT-5-[2-(4-carbmethoxyphenyl)ethen-1-yl]-2'-deoxyuridine
44: 5'-DMT-5-(4-acetoxybuten-1-yl)-2'-deoxyuridine
45: 5'-DMT-5-(4-acetoxybuten-1-yl)-2'-deoxyuridine
46: 5'-DMT-5-[4-(2,4-dinitrophenyl)butyl]-2'-deoxyuridine
is productive of the products wherein, $U^m$ is:
37a': 5-(propen-1-yl)uracil
38a': 5-(2-carboxyethyl)uracil
39': 5-(3-carboxypropan-1-yl)uracil
40': 5-(4-carboxy-2-methylbuten-1-yl)uracil
41': 5-(3-cyanopropen-1-yl)uracil 42': 5-(4-cyano-2-methylbuten-1-yl)uracil
43': 5-[2-(4-carboxyphenyl)ethen-1-yl]uracil
44': 5-(4-hydroxybuten-1-yl)uracil
45': 5-(4-hydroxybutan-1-yl)uracil
46': 5-[4-(2,4-dinitrophenyl)butyl]uracil Note: In 46' the dinitrophenyl is a ligand recognition type reporter group, i.e. use of antidinitrophenyl antibody as the ligand. Similarly, by employing other appropriate 5'-DMT-5-alkyl-2'-deoxyuridines, the analogous deoxyoligonucleotides are produced.

EXAMPLE XXI

Repeating the procedures of Examples XV to XVIII, but replacing 5'-DMT-5-(3-trifluoroacetylaminopropyl)-2'-deoxyuridine with 5'-DMT-$N^4$-benzoyl-5-(3-trichloroacetylaminopropyl)-2'-deoxycytidine is productive of deoxyoligonucleotides as in Example XVIII wherein $U^m$ [5-(3-aminopropyl)-uracil] is replaced by 5-(3-aminopropyl)cytosines. For example,

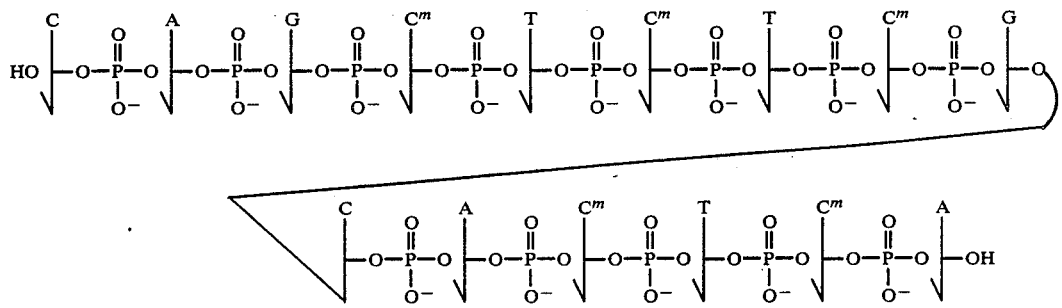

where $C^m$ = 5-(3-aminopropyl)cytosine.

EXAMPLE XXII

Repeating the deoxyoligonucleotide synthesis procedure of Example XXI but replacing 5'-DMT-$N^4$-5-(3-trichloroacetylaminopropyl)-2'-deoxycytidine with compounds numbered 47 through 57 below is productive of the corresponding oligonucleotides having the $C^m$ cytosine bases numbered 47' through 57' below, respectively, i.e., substituting:

47: 5-DMT-$N^4$-benzoyl-5-(3-trifluoroacetylaminopropen-1-yl)-2'-deoxycytidine
48: 5'-DMT-$N^4$-benzoyl-5-(4-trifluoroacetylaminobut-1-yl)-2'-deoxycytidine
49: 5'-DMT-$N^4$-benzoyl-5-(4-trifluoroacetylaminobuten-1-yl)-2'-deoxycytidine
50: 5'-DMT-$N^4$-benzoyl-5-(6-trifluoroacetylaminohex-1-yl)-2'-deoxycytidine
51: 5'-DMT-$N^4$-benzoyl-5-(6-trifluoroacetylaminohexen-1-yl)-2'-deoxycytidine
52: 5'-DMT-$N^4$-benzoyl-5-(3-trifluoroacetylaminoprop-2-yl)-2'-deoxycytidine
53: 5'-DMT-$N^4$-benzoyl-5-(3-trifluoroacetylamino-2-methylpropen-1-yl)-2'-deoxycytidine
54: 5'-DMT-$N^4$-benzoyl-5-(3-trifluoroacetylamino-2-methylprop-1-yl)-2'-deoxycytidine
55: 5'-DMT-$N^4$-benzoyl-5[2-(4-trifluoroacetylaminomethylphenyl)ethen-1-yl]-2'-deoxycytidine
56: 5'-DMT-$N^4$-benzoyl-5-[N-(pertrifluoroacetylpolylysyl)-1-acrylamido]-2'-deoxycytidine
57: 5'-DMT-$N^4$-benzoyl-5-[N-(trifluoroacetylaminoheptyl)acrylamido]-2'-deoxycytidine is productive of the products wherein $C^m$ is:

47': 5-(3-aminopropen-1-yl)cytosine
48': 5-(4-aminobut-1-yl)cytosine
49': 5-(4-aminobuten-1-yl)cytosine
50': 5-(6-aminohex-1-yl)cytosine
51': 5-(6-aminohexen-1-yl)cytosine
52': 5-(3-aminoprop-2-yl)cytosine
53': 5-(3-amino-2-methylpropen-1-yl)cytosine
54': 5-(3-amino-2-methylprop-1-yl)cytosine
55': 5-[2-(4-aminomethylphenyl)ethen-1-yl]cytosine
56': 5-[N-(polylysyl)-1-acrylamido]cytosine
57': 5-[N-(7-aminoheptyl)-1-acrylamido]cytosine Similarly, by employing other $N^4$-acyl-5-(acylaminoalkyl)-2'-deoxycytidines the analogous deoxyoligonucleotides are produced.

EXAMPLE XXIII

Repeating the deoxyoligonucleotide synthesis procedure of Example XXI, but replacing 5'-DMT-$N^4$-benzoyl-5-(3-trifluoroacetylaminopropyl)-2'-deoxycytidine with the compounds numbered 58 through 68 below is productive of the corresponding oligonucleotides having the $C^m$ cytosine bases numbered 58' through 68' below, respectively, i.e., substituting:

58: 5'-DMT-$N^4$-benzoyl-5-(propen-1-yl)-2'-deoxycytidine
59: 5'-DMT-$N^4$-benzoyl-5-(2-carbmethoxyethyl)-2'-deoxycytidine
60: 5'-DMT-$N^4$-benzoyl-5-(2-carbmethoxyethen-1-yl)-2'-deoxycytidine
61: 5'-DMT-$N^4$-benzoyl-5-(3-carbmethoxyprop-1-yl)-2'-deoxycytidine
62: 5'-DMT-$N^4$-benzoyl-5-(4-carbmethoxy-2-methylbuten-1-yl)-2'-deoxycytidine
63: 5'-DMT-$N^4$-benzoyl-5-(3-cyanopropen-1-yl)-2'-deoxycytidine
64: 5'-DMT-$N^4$-benzoyl-5-(4-cyano-2-methylbuten-1-yl)-2'-deoxycytidine
65: 5'-DMT-$N^4$-benzoyl-5-[2-(4-carbmethoxyphenyl)ethen-1-yl]-2'-deoxycytidine
66: 5'-DMT-$N^4$-benzoyl-5-(4-acetoxybuten-1-yl)-2'-deoxycytidine
67: 5'-DMT-$N^4$-benzoyl-5-(4-acetoxybut-1-yl)-2'-deoxycytidine
68: 5'-DMT-$N^4$-benzoyl-5-[4-(2,4-dinitrophenyl)butyl]-2-deoxycytidine is productive of the products wherein $C^m$ is:

58': 5-(propen-1-yl)cytosine
59': 5-(2-carboxyethyl)cytosine
60': 5-(2-carboxyethen-1-yl)cytosine
61': 5-(3-carboxyprop-1-yl)cytosine
62': 5-(4-carboxy-2-methylbuten-1-yl)cytosine
63': 5-(3-cyanopropen-1-yl)cyostine
64': 5-(4-cyano-2-methylbuten-1-yl)cytosine 65': 5-[2-(4-carboxyphenyl)ethen-1-yl]cytosine
66': 5-(4-hydroxybuten-1-yl)cytosine
67': 5-(4-hydroxybut-1-yl)cytosine
68': 5-[4-(2,4-dinitrophenyl)butyl]cytosine Similarly, by employing other appropriate 5'-DMT-N⁴-acyl-5-alkyl-2'-deoxycytidines the analogous deoxyoligonucleotides are produced.

EXAMPLE XXIV

Repeating the phosphomonochloridite and deoxyoligonucleotide synthesis procedures of Examples XV–XXIII, but replacing 5'-DMT-5-(3-trifluoroacetylaminopropyl)-2'-deoxyuridine with 5'-DMT-N⁶-benzoyl-8-(6-trifluoroacetylaminohexyl)amino-2'-deoxyadenosine is productive of deoxyoligonucleotides as in Example XVIII, except that the $U^m$ is replaced by $A^m$, and $A^m$=8-(6-aminohexyl)amino-2'-deoxyadenosine.

Examples XXVI to XXIX typify the binding of reporter groups to oligonucleotides containing appropriately modified bases, as illustrated in Reaction 6.

EXAMPLE XXV

Fluoresceinated deoxyoligonucleotides

A purified pentadeca-nucleotide (from Example XVIII) of the structure

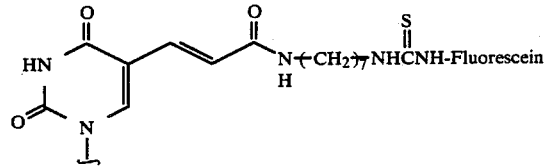

or unreacted 5-[N-(7-aminoheptyl)-1-acrylamido]uracil. $\lambda_{max}$ (H₂O)

262 nm, 498 nm.

Repeating the procedure on compounds recited in Examples XIX, XXI, XXII, and XXIV is productive of the corresponding fluoresceinated or polyfluoresceinated deoxyoligonucleotides in like manner.

EXAMPLE XXVI

Attachment of reporter groups other than fluorescein can be accomplished by repeating the procedure of Example XXV, but replacing fluorescein isothiocyanate with, for example:

2,4-dinitrophenyl isothiocyanate
1-fluoro-2,4-dinitrobenzene
aminoethyl isoluminol isothiocyanate

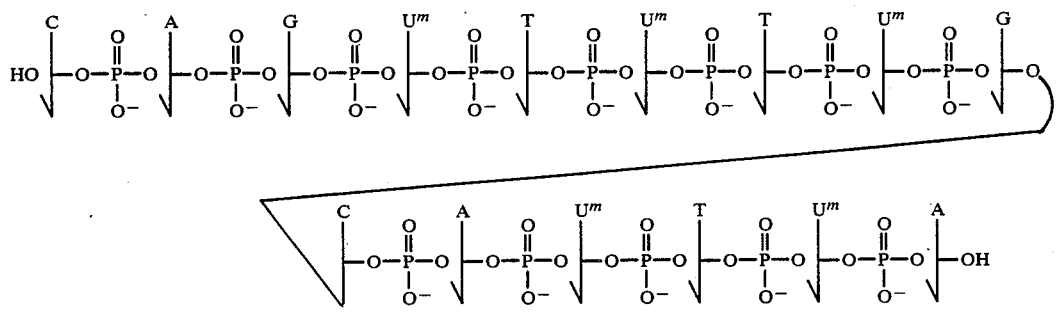

[where $U^m$ is 5-[N-(7-aminoheptyl)-1-acrylamido]uracil is dissolved at 25 A₂₆₀ units per ml in aqueous 300 mM sodium borate or sodium carbonate buffer, pH 9.5, containing 30 mM sodium chloride. Solid fluorescein isothiocyanate (0.5 mg per ml) is added, and the mixture sealed and shaken gently at 4° C. to 25° C. overnight. The reaction is chromatographed directly on a column of G-50 Sephadex ® to separate unbound fluorescein adducts which are retained; the fluoresceinated deoxyoligonucleotide adducts elute near the void volume. Early fractions containing significant A₂₆₀ units are combined and lyophilized to solid product of structure similar to the starting petadecadeoxyoligonucleotide where $U^m$ is now either aminoethylaminonaphthalene-1,2-carboxylic hydrazide isothiocyanate
N,N'-bis (alkylsulfonyl)-N-aryl-N'-isothiocyanatoaryldioxamide
m-sulfonyl aniline isothiocyanate
N-hydroxysuccinimidyl biotin
9-(n-hydroxysuccinimidyl carboxy)-N-methylacridine,
or cyanogenbromide-activated Sepharose ® is productive of the corresponding adducts wherein the attached group is other than fluorescein.

EXAMPLE XXVII

Attachment of isoluminol and free primary amine-containing reporter groups

A purified pentadecanucleotide from Example XVIII of the structure:

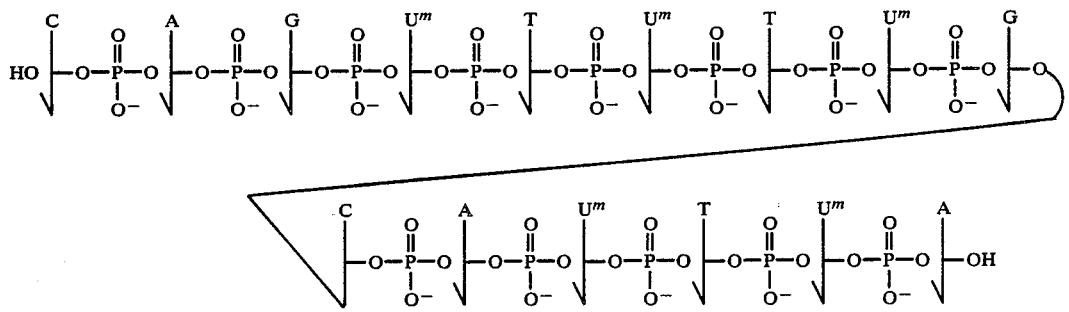

[where $U^m$ is 5-(2-carboxyethenyl)uracil] is dissolved in water at 30 $A_{260}$ units per ml, and diluted with one volume pyridine. Aminobutyl ethyl isoluminol is added to a final concentration of 1 mg/ml, followed by addition of a five-fold molar excess of 1-ethyl-3-(3-dimethylaminopropyl)carbodiimide. The reaction is sealed and shaken gently in the dark for 12 to 48 hours. The reaction mixture is concentrated under reduced pressure to a solid residue, and chromatographed directly on a column of G-50 Sephadex ®; the isoluminol-deoxyoligonucleotide conjugates elute near the void volume. Early fractions containing significant $A_{260}$ units are combined and lyophilized to solid product of structure similar to the starting deoxyoligonucleotide where $U^m$ is now either:

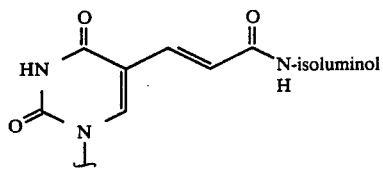

or unreacted 5-(2-carboxyethenyl)uracil.

Repeating the procedure on compounds from Examples XVI and XXIV wherein $R_2$ contains carboxy is productive of the corresponding deoxyoligonucleotide-isoluminol adducts in like manner.

Repeating the procedure, but replacing aminobutyl isoluminol with other reporter groups containing a free primary amine is productive of the corresponding deoxyoligonucleotide-reporter adducts in like manner.

EXAMPLE XXVIII

Attachment Of Dinitrophenyl Reporter Groups

A purified nanonucleotide of the structure:

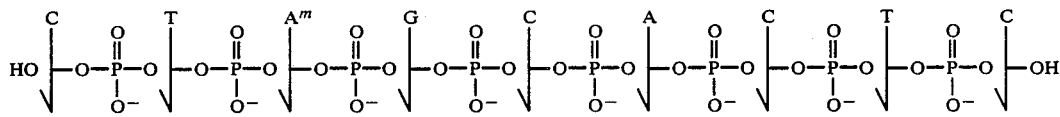

where $A^m$ = 8-(6-aminohexyl)aminoadenine is dissolved at 20 $A_{260}$ units per ml in 250 mM sodium carbonate buffer, pH 9, and 1-fluoro-2,4-dinitrobenzene is added. The reaction solution is shaken at ambient temperature overnight, then chromatographed directly on a column of Sephadex ® G-50. Early fractions containing significant $A_{260}$ units are combined and concentrated to give an oligonucleotide product similar to the starting decanucleotide wherein $A^m$ is now either:

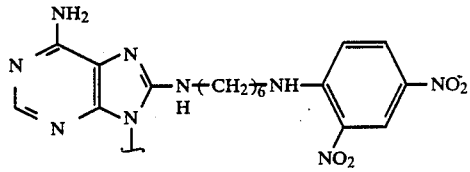

or unreacted 8-(6-aminohexyl)aminoadenine.

Repeating the procedure, but replacing 8-(6-aminohexyl)aminoadenine with other modified bases containing a free primary amine, is similarly productive of the corresponding dinitrophenylated oligonucleotide adducts.

EXAMPLE XXIX

Preparation of 5'-DMT-5-[N-trifluoroacetylaminoheptyl) 1-acrylamido]-2'-deoxyuridine methyl N,N-diisopropylphosphoramidite.

The method followed was that of Beaucage and Caruthers, (1981). Tet. Lett. 22:1859, with some modification. Dry 5'-DMT-5-[N-trifluoroacetylaminoheptyl)1-acrylamido]-2'-deoxyuridine (3.0 g, 3.7 mmol) from Example II was dissolved in 12 ml dichloromethane in a dry 50 ml round bottom flask with a septum cap. The flask was flushed with argon gas and evacuated several times to remove residual water vapor. 2.1 ml triethylamine was added with a dry syringe, and the mixture cooled to 0° C. While stirring, 1.44 ml N,N-diisopropyl-methylphosphoramidic chloride was added drop-wise with a syringe. The mixture was allowed to warm to room temperature and stirred 30 minutes. 20 ml ethyl acetate was added, the contents were mixed, and extracted with 50 ml cold aqueous NaCl (saturated). The aqueous phase was re-extracted two times with ethyl acetate. The ethyl acetate phases were combined and dried over sodium sulfate, then carefully concentrated to dryness. Crude product was purified on a well-equilibrated and neutralized silica column (1.5×75 cm), eluting triethylamine/cycclohexane/ethylacetate (1:50:150). The resulting product was concentrated to dryness, and lyophilized from pyridine/benzene (1:99) to give product nucleoside amidite as a fluffy white solid (2.6 g, 72% recovery) which had the following characteristics:

UV (methanol): λ max 302 nm (ε 18,400), 288 nm, 236 nm (ε 25,700)

TLC (plates prewashed TEA/EtOAc 1:49): Rf=0.45, 0.55 (diasteriomers) (EtOAc/cyclohexane 2:1).

Elemental analysis (C, H, N, P, F): +0.6%. P-NMR: S 149.1, 149.5 (diasteriomers).

This modified nucleoside amidite most closely resembles thymidine in structure and in hybridization characteristics, and can be substituted in place of one or more thymidines for oligonucleotide synthesis.

EXAMPLE XXX

Preparation of 5'-DMT-5-[N-trifluoroacetylaminoheptyl)-1-acrylamido]-2'-deoxyuridine Beta-cyanoethyl N,N-diisopropylphosphoramidite.

The procedure of Example XXIX was followed using N,N-diisopropyl-(2-cyanoethyl) phosphoramidic chloride as the phosphitylating agent. The resulting product had the following characteristics:

UV: identical to that of product of Example XXIX

TLC: (plates prewashed TEA/EtOAc 1:49) Rf=0.35 0.48 (diasteriomers) (EtOAc/cyclohexane 2:1))

Elemental Analysis (C, H, N, P, F): ±0.3%

EXAMPLE XXXI

Synthesis of Linker Arm Oligonucleotides by Phosphoramidite Methodology

Phosphoramidite synthesis was accomplished using an Applied Biosystems, Inc. (ABI) model 380A programmable DNA synthesizer in accordance with the manufacturer's instructions. As is well known, DNA synthesizers selectively mix different synthesis reagents according to a predetermined time and volumetric program. To achieve this, the several reagents were stored in containers, each having a valved exit to a mixing chamber The outlet valves were selectively and automatically opened to admit the reagent to the mixing chamber in accordance with a computer controlled sequence. The program utilized was based substantially on the phosphoamidite synthesis protocol of Caruthers, et. al. (1981). *J. Am. Chem. Soc.* 103:3185. Prior to synthesis, 20 mg for each condensation of modified nucleoside amidite as prepared in Examples XXIX or XXX was weighed into the amidite bottle, lyophilized from pyridine/benzene overnight, and dissolved in 150 μl dry acetonitrile per 20 mg modified nucleoside amidite. The modified nucleoside amidite bottle was connected to the synthesizer and the desired sequences, chosen to be complementary to the nucleic acid sequence chosen for hybridization, programmed into the machine. The desired program substitutes the modified nucleoside amidite in place of one or more thymidines. Coupling efficiencies of the modified nucleotide were indistinguishable from standard amidites, and averaged greater than 98% by measurement of DMT releases To allow purification of the product oligonucleotide by HPLC, the chosen program left DMT attached to the product.

After synthesis was completed, standard cleavage methods (1 hour thiophenol for methyl amidites, ammonium hydroxide treatment) were used. Deprotection in ammonium hydroxide was 2 hours at ambient temperature, then 50° C. for 15 hours. The crude oligonucleotide solution was concentrated carefully to a small volume (<500 μl) in the presence of tributylamine. The DMT crude was analyzed by analytical reverse phase high pressure liquid chromatography (RPHPLC) and purified by preparatory RPHPLC. Those fractions containing the DMT-oligomer were combined, concentrated to dryness, and treated with 80% acetic acid for 40 minutes at ambient temperature to remove DMT. The product was desalted on a 1×30 cm column of Sephadex RG-25 (fine), (Pharmacia Fine Chemicals, Piscataway, N.J.) and ethanol precipitated from 300 mM sodium acetate, pH 7. Analysis by PAGE both by kinasing and autoradiography, and by Stains-all (Aldrich Chemical Co., Milwaukee, Wis.) developed gels indicating a single homogeneous band.

EXAMPLE XXXII

Preparation of Fluorescent Linker Arm Oligonucleotides

To a solution of 300 μg linker arm oligonucleotide (8.1 OD260, 50 nmol, prepared by the method of Example XXXI) in 250 μl 1 500 mM sodium bicarbonate, pH 9.4, was added 8.6 mg FITC solid. The solution was agitated at room temperature for 6 hours The product oligonucleotide was separated from unreacted FITC using 1×30 cm Sephadex ® G-25 column eluting 20 mM ammonium acetate, pH 6 Fractions in the first UV-absorbing peak were combined. Analysis by analytical 20% PAGE indicated reaction was complete, with fluroescent oligomer electrophoresing slower by the equivalent of 1 nucleotide unit. The FITC-oligomer was purified by preparatory RPHPLC detecting simultaneously at 260 and 495 nm. The product was concentrated and ethanol precipitated to recover 4.8 OD260 (55%) of fluoresceinated oligonucleotide. Products were found to be homogeneous by PAGE and RPHPLC, to kinase normally, and to have UV-vis absorbance ratios predicted for specific oligomer-fluorophore conjugates. These fluorescent linker arm oligonucleotides are used directly for hybridization to nucleic acids to determine the presence of complementary sequence.

EXAMPLE XXXIII

Preparation Of Linker Arm Oligonucleotide-alkaline Phosphatase Conjugates

Twenty-five microliters of linker arm oligonucleotide (14 nMol) at a concentration of 4 mg/ml in 0.1M sodium bicarbonate and 2 mM EDTA was combined with 50 μl solution of disuccinimidyl suberate (DSS) (1.4 μmol) at a concentration of 10 mg/ml in dimethyl sulfoxide. The reaction was allowed to proceed for 5 minutes at room temperature in the dark, then immediately applied to a Sephadex ® G-25 column, 1 cm×40 cm, and eluted at 4° C. with water. The eluted fractions (0.5 ml) were monitored by absorbance at 260 nm. The first peak fractions, containing activated linker arm oligonucleotide, were pooled and frozen for lyophilization as quickly as possible to minimize hydrolysis of reactive succinimidyl groups. Unreacted DSS and products were well resolved from the modified oligomer fractions. The lyophilized and modified linker arm oligomer was rehydrated with a two-fold stoichiometric excess of alkaline phosphatase (4 mg) in 200 μl of 0.1M sodium bicarbonate, 3M NaCl, 0.05% sodium azide, pH 8.25. The conjugation reaction mixture was maintained at room temperature for 16 hours. The products of the conjugation reaction were separated by gel filtration chromatography using a 1×100 cm column of P-100 (Bio Rad, Richmond, Calif.) eluting 50 mM Tris, pH 8.5, at 4° C. The protein containing fractions were pooled and dialyzed against 50 mM tris, pH 8.5, in the cold. Pure oligomer-alkaline phosphatase conjugate was obtained by chromatography on a 1 ×6 cm column of DEAE cellulose eluting 0.1 mM Tris in 0.1M NaCl. The peak fractions were pooled and concentrated to approximately 1 mg/ml protein by vacuum dialysis against 50 mM tris, pH 8.5, and stored at 4° C. in the presence of 0.05% sodium azide. Alkaline phosphatase retained full enzymatic activity, 400–500 U/mg protein, as determined by spectrophotometric assay, throughout the conjugation and purification processes. The overall yield with respect to oligomer was approximately 30–50%.

Although the invention has been described with reference to specific examples, it should be understood that various modifications can be made without departing from the spirit of the invention. Accordingly the invention is limited only by the following claims.

I claim:

1. A compound useful as an intermediate in the chemical synthesis of a single-stranded oligonucleotide comprising the structure:

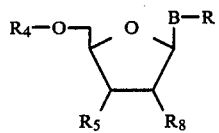

wherein
B is a pyrimidine or purine base;
R is a linker arm attached to a compound selected from the group consisting of a blocking group, a detectable label and a solid surface;
and provided that when $R_4$ = blocking group then
$R_5$ = reactive phosphorus containing group
or
= H if the 5' —OH group of the 5'-terminal nucleotide of a growing oligonucleotide contains a reactive phosphorous-containing group, and when $R_5$ = blocking group then
$R_4$ = reactive phosphorous-containing group
or
= H if the 3' —OH group of the 3'-terminal nucleotide of a growing oligonucleotide contains a reactive phosphorus-containing group; and
$R_8$ = H.

2. The compound of claim 1 wherein R is

—$CH_2CHR_1C_nH_{2n}Y$;

—$CH=CR_1C_nH_{2n}Y$;

—$CHR_1C_nH_{2n}Y$;

or

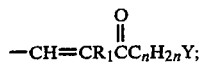

Wherein $R_1$ is H or alkyl, n is 0 to 20 and Y contains a blocked amino or blocked carboxyl or blocked hydroxy or blocked thio group or a reporter group or a solid support.

3. The modified nucleoside monomer of claim 1 wherein R is attached at a sterically tolerant site.

4. The modified nucleoside monomer of claim 1 wherein R is attached at the C-5 position when B is a pyrimidine or the C-8 position when B is a purine.

* * * * *

UNITED STATES PATENT AND TRADEMARK OFFICE
CERTIFICATE OF CORRECTION

PATENT NO. : 4,948,882
DATED : August 14, 1990
INVENTOR(S) : Jerry L. Ruth

It is certified that error appears in the above-indentified patent and that said Letters Patent is hereby corrected as shown below:

Column 43:
Claim 1, lines 35 through 39, should read

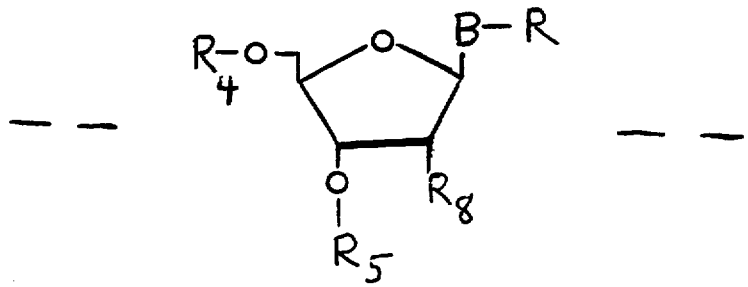

Signed and Sealed this

Twenty-third Day of January, 1996

Attest:

BRUCE LEHMAN

Attesting Officer

Commissioner of Patents and Trademarks